(12) United States Patent
Pelletier et al.

(10) Patent No.: US 9,157,311 B2
(45) Date of Patent: Oct. 13, 2015

(54) METHOD AND SYSTEM OF DETERMINING CONSTITUENT COMPONENTS OF A FLUID SAMPLE

(75) Inventors: Michael T. Pelletier, Houston, TX (US); Christopher M. Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/808,035

(22) PCT Filed: Jul. 8, 2010

(86) PCT No.: PCT/US2010/041273
§ 371 (c)(1),
(2), (4) Date: Jan. 2, 2013

(87) PCT Pub. No.: WO2012/005725
PCT Pub. Date: Jan. 12, 2012

(65) Prior Publication Data
US 2013/0104642 A1    May 2, 2013

(51) Int. Cl.
*E21B 47/00*    (2012.01)
*E21B 49/10*    (2006.01)
(Continued)

(52) U.S. Cl.
CPC .............. *E21B 47/00* (2013.01); *E21B 49/10* (2013.01); *G01N 21/1702* (2013.01); *G01N 33/2823* (2013.01)

(58) Field of Classification Search
CPC ....... E21B 47/00; E21B 47/101; E21B 44/00; E21B 49/08

USPC ...................................................... 73/152.47
See application file for complete search history.

(56) References Cited

U.S. PATENT DOCUMENTS 4,187,026 A    2/1980    Schaffer et al.
4,492,862 A    1/1985    Grynberg et al.
(Continued)

FOREIGN PATENT DOCUMENTS

CA       1186402 A1    4/1985
WO    2006/063094       6/2006
(Continued)

OTHER PUBLICATIONS

International Search Report issued Mar. 29, 2011 in International Application No. PCT/US2010/041273.
(Continued)

*Primary Examiner* — Hezron E Williams
*Assistant Examiner* — Tarun Sinha

(57) ABSTRACT

Determining constituent components of a fluid sample. At least some of the illustrative embodiments are methods including: creating electromagnetic energy with a wavelength in the infrared region; directing the electromagnetic energy into a fluid sample; modulating the electromagnetic energy at a modulation frequency; directing the electromagnetic energy that passes through the fluid sample to a first resonant chamber, the first resonant chamber has an acoustic resonant frequency substantially equal to the modulation frequency; absorbing at least a portion of the electromagnetic energy by a detector fluid within the first resonant chamber; detecting acoustic energy within the first resonant chamber; and determining a first constituent component of the fluid sample based on the acoustic energy within the first resonant chamber.

37 Claims, 14 Drawing Sheets

(51) Int. Cl.
*G01N 21/17* (2006.01)
*G01N 33/28* (2006.01)

(56) References Cited

U.S. PATENT DOCUMENTS

| | | | |
|---|---|---|---|
| 5,159,411 | A | 10/1992 | Hammerich et al. |
| 5,596,146 | A | 1/1997 | Waller et al. |
| 6,466,806 | B1 | 10/2002 | Geva et al. |
| 6,608,683 | B1 * | 8/2003 | Pilgrim et al. ............. 356/432 |
| 6,729,185 | B2 | 5/2004 | Autrey et al. |
| 6,873,415 | B2 | 3/2005 | Amonette et al. |
| 7,069,769 | B2 | 7/2006 | Kung |
| 7,165,451 | B1 | 1/2007 | Brooks et al. |
| 7,263,871 | B2 | 9/2007 | Selker et al. |
| 7,387,021 | B2 | 6/2008 | DiFoggio |
| 7,423,258 | B2 | 9/2008 | DiFoggio |
| 7,520,158 | B2 | 4/2009 | DiFoggio |
| 7,614,302 | B2 | 11/2009 | DiFoggio et al. |
| 7,663,756 | B2 | 2/2010 | Cole |
| 7,671,983 | B2 | 3/2010 | Shammai et al. |
| 2005/0070803 | A1 | 3/2005 | Cullum et al. |
| 2007/0167832 | A1 | 7/2007 | Yaniv et al. |
| 2008/0149819 | A1 * | 6/2008 | Zhdaneev ............... 250/255 |
| 2008/0196477 | A1 | 8/2008 | Van Herpen et al. |
| 2008/0198364 | A1 | 8/2008 | Willing et al. |
| 2009/0128819 | A1 | 5/2009 | Van Kesteren et al. |
| 2009/0229345 | A1 | 9/2009 | Van Kesteren |
| 2010/0045991 | A1 | 2/2010 | Miklos et al. |
| 2010/0045998 | A1 | 2/2010 | Fritz et al. |

FOREIGN PATENT DOCUMENTS

| | | |
|---|---|---|
| WO | 2006/114766 | 11/2006 |
| WO | 2007/098034 | 8/2007 |
| WO | 2009/007875 A2 | 1/2009 |

OTHER PUBLICATIONS

Arnott, W. Patrick et al. Photoacoustic Spectrometer for Measuring Light Absorption by Aerosol: Instrument Description. Atmospheric Environment 33; pp. 2845-2852. 1999.

Firebaugh, Samara L et al. Miniaturization and Integration of Photoacoustic Detection with a Microfabricated Chemical Reactor System. J. Microelectromechanical Syst. vol. 10, No. 2. Jun. 2001.

Harren, Frans J.M. et al. Photoacoustic Spectroscopy in Trace Gas Monitoring. Encyclopedia of Analytical Chemistry. R.A. Meyers, Ed. pp. 2203-2226. John Wiley & Sons, Ltd., Chichester. 2000.

Kim, J.W. et al. A New Development of Photoacoustic Detection for Microship-CE Using a Simple Pick-Up Device (abstract only). International Journal of Thermophysics. vol. 29, No. 6. Dec. 2008. Published online Jul. 25, 2008.

\* cited by examiner

METHOD AND SYSTEM OF DETERMINING CONSTITUENT COMPONENTS OF A FLUID SAMPLE

BACKGROUND

Hydrocarbon drilling and production operations demand a great quantity of information relating to parameters and conditions downhole. Such information may comprise characteristics of the earth formations traversed by the borehole, as well as characteristics of the various fluids within the earth formations traversed by the borehole. Systems for measuring conditions downhole, including the movement and location of the drilling assembly contemporaneously with the drilling of the well, have come to be known as "measurement-while-drilling" techniques, or "MWD". Similar techniques, concentrating more on the measurement of formation parameters, have come to be known as "logging while drilling" techniques, or "LWD". While distinctions between MWD and LWD may exist, the terms MWD and LWD often are used interchangeably. For purpose of this disclosure, the term MWD will be used with the understanding that this term encompasses both the collection of formation parameters and the collection of information relating to the movement and position of the drilling assembly. In other situations, the parameters and conditions downhole may be detected by wireline devices placed in the borehole after the drill string has been removed or "tripped".

Many difficulties exist in performing MWD, such as limited space in which to perform testing and the conditions experienced downhole. For example, the temperature in deep hydrocarbon wells may reach or exceed 450 degrees Fahrenheit. Electronic devices designed and constructed for temperature ranges expected for surface applications may have severely reduced performance at expected downhole temperature, and in many cases are inoperable at expected downhole temperatures. The temperature operability problem is particularly pronounced for devices used to detect electromagnetic radiation, such as may be used in downhole spectroscopy.

Thus, any advance which overcomes difficulties relating to operation of devices at elevated temperature would provide a competitive advantage in the industry.

BRIEF DESCRIPTION OF THE DRAWINGS

For a detailed description of exemplary embodiments, reference will now be made to the accompanying drawings in which.

NOTATION AND NOMENCLATURE

Certain terms are used throughout the following description and claims to refer to particular system components. As one skilled in the art will appreciate, energy service companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . . " Also, the term "couple" or "couples" is intended to mean either an indirect or direct connection. Thus, if a first device couples to a second device, that connection may be through a direct connection or through an indirect connection via other devices and connections.

"Chopping" and "modulation", with respect to electromagnetic energy, shall mean a periodic decrease in the intensity of electromagnetic energy, but shall not be read to require a decrease to zero intensity of the electromagnetic signal.

"Substantially" shall mean, with respect to the relationship between two frequencies, the frequencies are within 20 Hertz of each other.

"Substantially" shall mean, with respect to the relationship between two fluid flow rates, the fluid flow rates are within 5% of each other.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1A:
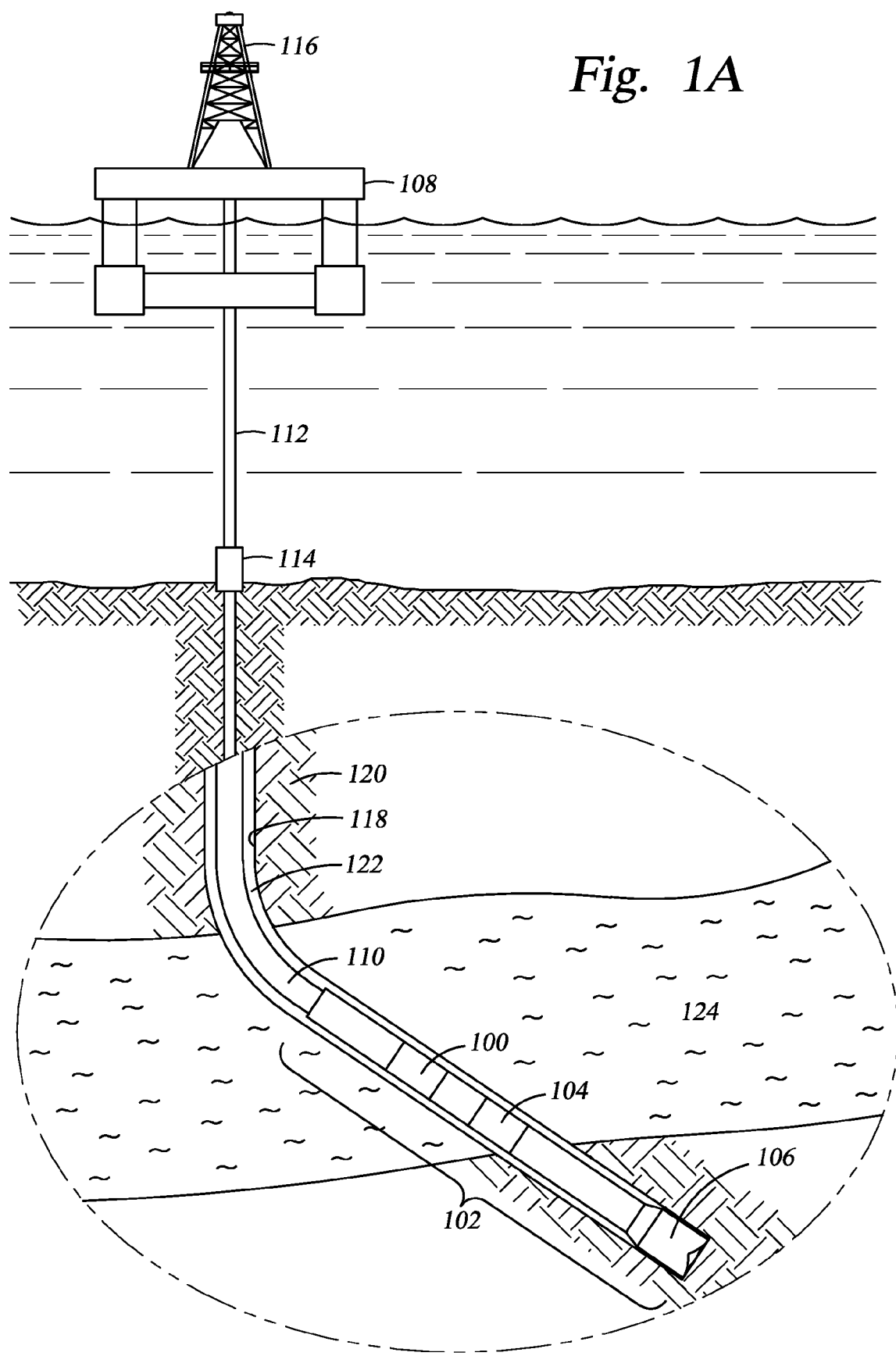
FIG. 1A shows a drilling system in accordance with at least some embodiments.

Referring initially to FIG. 1A, a MWD formation evaluation or formation fluid identification tool 100 is shown schematically as a part of bottom hole assembly 102 which comprises an MWD sub 104 and a drill bit 106 at the distal end. The bottom hole assembly 102 is lowered from a drilling platform 108, such as a ship or other drilling platform, by way of a drill string 110. The drill string 110 extends through a riser 112 and a well head 114. Drilling equipment supported within and around derrick 116 rotates the drill string 110 and the drill bit 106, causing the bit 106 to form a borehole 118 through the formation material 120. The volume defined between the drill string 110 and the borehole 118 is referred to as the annulus 122. The borehole 118 penetrates subterranean zones or reservoirs, such as reservoir 124, that are believed to contain hydrocarbons in a commercially viable quantity. It is also consistent with the teachings herein that the tool 100 is employed in other bottom hole assemblies and with other drilling apparatus in land-based drilling with land-based platforms, as well as offshore drilling as shown in FIG. 1. In addition to the MWD tool 100, the bottom hole assembly 102 may also contain various other systems, such as a down hole drill motor, a rotary steerable tool, a mud pulse telemetry system, and other MWD sensors and systems.

In some embodiments, the information gathered by the tool 100 may be stored within the tool 100 and read when the tool 100 is raised to the surface or the platform 108. In other embodiments, some or all the information gathered by the tool may be sent to the surface or platform 108 while the tool 100 is within the borehole 118. For example, some or all the information gathered by the tool 100 may be sent encoded in pressure pulses in the drilling fluid within the drill string 110. In yet still other embodiments, the information gathered by the tool 100 may be sent over a communication pathway embedded within the pipes of the drill string 110, such as by electrical conductors or optical conductors.

Figure 1B:
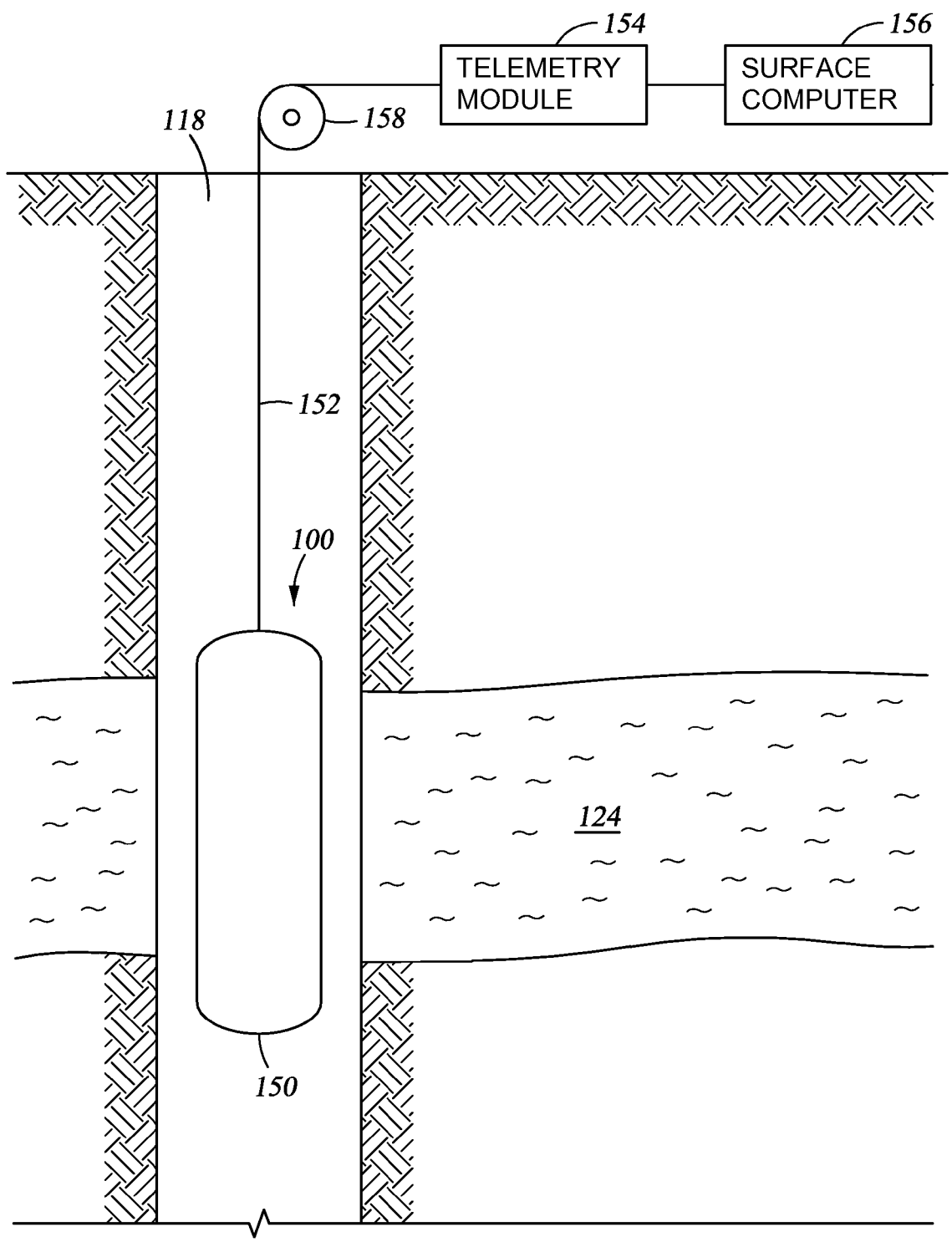
FIG. 1B shows a wireline system in accordance with at least some embodiments.

While in some embodiments the formation fluid identification tool is used in drilling operations, in yet still other embodiments of the formation fluid identification tool is used in wireline logging operations. In particular, FIG. 1B illustrates a wireline logging system that comprises a logging tool 100 placed within a borehole 118 proximate to the reservoir 124 of interest. The tool 100 comprises a pressure vessel 150 within which various subsystems of the tool 100 reside, and in the illustrative case of FIG. 1B the pressure vessel 150 is suspended within the borehole 118 by a cable 152. Cable 152, in some embodiments a multi-conductor armored cable, not only provides support for the pressure vessel 150, but also in these embodiments communicatively couples the tool 100 to a surface telemetry module 154 and a surface computer 156. The tool 100 may be raised and lowered within the borehole 118 by way of the cable 152, and the depth of the tool 100 within the borehole 118 may be determined by depth measurement system 158 (illustrated as a depth wheel).

Figure 2:
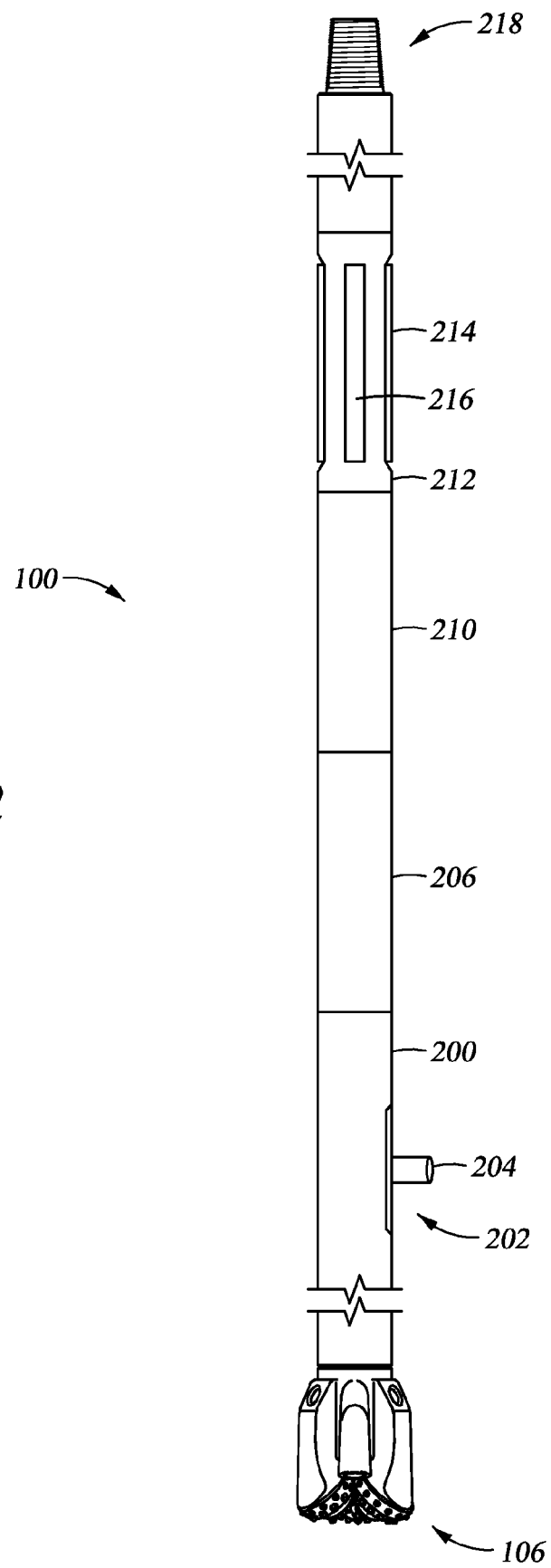
FIG. 2 shows a fluid identification tool in accordance with at least some embodiments.

FIG. 2 shows an exemplary embodiment of the tool 100 in a MWD configuration. A first end of the tool 100 includes a probe section 200. For reference purposes, the first end of the tool 100 at the probe section 200 is in some embodiments the lowermost end of the tool, which is closest to the drill bit 106. The probe section 200 comprises a probe assembly 202 having an extendable sample device or extendable probe 204 (shown in an extended orientation). During periods of time when the drill string is turning, the extendable probe 204 is withdrawn into the probe assembly 202. When the formation is to be tested, or when a sample of formation fluid is desired, rotation of the drill string is stopped and the probe 204 is extended to contact and seal against the borehole. Thereafter formation fluids are drawn into the tool 100. In situations where a sample of the drilling fluid in the annulus is desired, the drilling fluid may be drawn into the probe 204 without extension.

The tool 100 also comprises a power section 206 coupled to the probe section 200. The operative connection between the probe section 200 and the power section 206 comprises fluid and power/electrical pass-through capabilities, such as for electrical signals, power, and formation fluids drawn through the probe 204. Though not specifically illustrated, power section 206 comprises components such as a pump assembly which draws fluids into the tool 100 through probe 204, a flow gear or turbine assembly from which electrical power for use by the tool may be generated by the drilling fluid flowing through the tool 100, and an electronics module which controls operation of the various pumps and valves.

Still referring to FIG. 2, a test section 210 is coupled to the power section 206. The test section 210 is or comprises a pressure vessel that houses the various components used to measure and/or determine constituent components of the formation fluid drawn in the probe 204 (the testing described more thoroughly below). A sample bottle section 212 may be coupled to the test section 210. The sample section 212 may include one or more sample bottle assemblies 214, 216 within which samples of the formation fluids may be stored for more detailed analysis at the surface. The entire tool couples by threads 218 to the balance of the bottom hole assembly 102.

Figure 3:
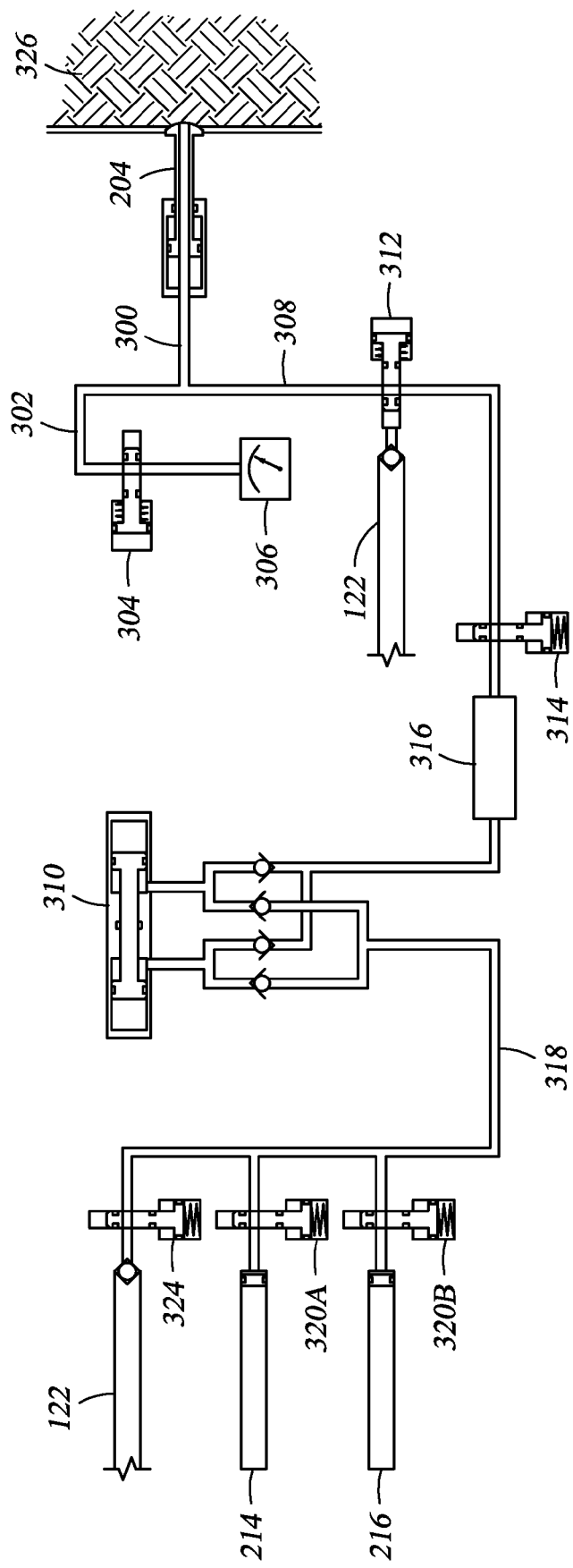
FIG. 3 shows a fluid schematic of a fluid identification tool in accordance with at least some embodiments.

FIG. 3 shows, schematically, illustrative fluid connections within the tool 100. The various components illustrated span several sections (e.g., the sample bottle assemblies on the left of the figure reside within the sample bottle section 212, while the probe 204 on the right resides within the probe section 200); however, the components are shown together as a single integrated system so as not to unduly complicate the figure. In particular, the system comprises sample probe 204 fluidly coupled to a flow line 300. Flow line 300 couples to a test branch 302 comprising valve 304 and meter 306, and flow line 300 also couples to a flow line 308. Each flow line branch will be discussed in turn.

Flow line 302 couples to shut-in valve 304 and meter 306. When shut-in valve 304 is closed, the meter 306 is fluidly isolated from the probe 204. However, when shut-in valve 304 is opened, the meter 306 is fluidly coupled to the probe 204 such that any suitable measurement can be made. For example, in some embodiments meter 306 is a pressure meter, which thus measures the pressure of the formation fluid to which the probe 204 is fluidly coupled. Such measurements can be made both when the pump 310 (discussed below) is operational, and when pump 310 is fluidly isolated from the probe 204.

Still referring to FIG. 3, flow line 308 couples to a plurality of components, including equalizing valve 312, flow line shut-off valve 314, spectroscopic sensor system 316, drawdown pump 310 and flow line 318. When desired to equalize the pressure in the probe 204 to that of the borehole, shut off valve 314 is closed and equalizing valve 312 is opened, thus equalizing the pressure to that of annulus 122. Flow line 318 fluidly couples, in turn, to one or more bottle valves 320, which bottle valves couple to respective sample bottle assemblies 214, 216. Flow line 318 also couples to vent valve 324. Vent valve 324 selectively vents flow line 318 to the annulus 122.

During periods of time when a formation test is being performed, equalizing valve 312 is closed, flow line shut off valve 314 is opened, pump 310 is operated to draw fluids, and vent valve 324 is open, thus creating a flow path through the system. Initially the various flow lines carry the fluid within the bore hole (e.g., drilling fluid), based in part on the fluids within the bore hole entering the probe when retracted, and/or drawing portions of those fluids that have penetrated or invaded the formation 326. Eventually, however, the fluids moving through the various flow lines will be almost exclusively formation fluids.

Various tests can be performed on the formation and the formation fluid using the illustrative system of FIG. 3. For example, for a draw-down test the test valve 304 may be opened, and the pressure within the flow line read by sensor 306 as the pump 310 draws fluids through the tool. Further still, with sensor 306 fluidly coupled to the probe 204 and fluids flowing, flow line shut off valve 314 may be closed, and the amount of time the formation takes to return to an original and/or static pressure may be determined. In some cases samples of the fluid within the flow lines (and thus samples of the fluid in the bore hole and/or formation fluid) may be taken and stored. For example, valve 320A may be opened during a draw-down test, and vent valve 324 closed, thus forcing fluid into sample bottle 214. Thereafter, valve 320A is closed and vent valve 324 is opened again. At a later time within the particular draw-down test, or perhaps a different test at a different depth in the bore hole, valve 320B is opened and vent valve 324 is closed, thus forcing fluid into sample bottle 216. The sample bottles may be removed at the surface, and the fluids therein analyzed in a laboratory.

Yet further still, with valve 314 open and pump 310 drawing fluids, as the fluids flow through sensor system 316 various parameters may be measured, such as a determination as to some or all the constituent components of the fluid. In accordance with the various embodiments, the sensor system 316 determines constituent components of the fluids based on electromagnetic energy absorption characteristics of the fluid, and how electromagnetic energy that passes through the fluids interacts with an acoustic resonant chamber.

Figure 4:
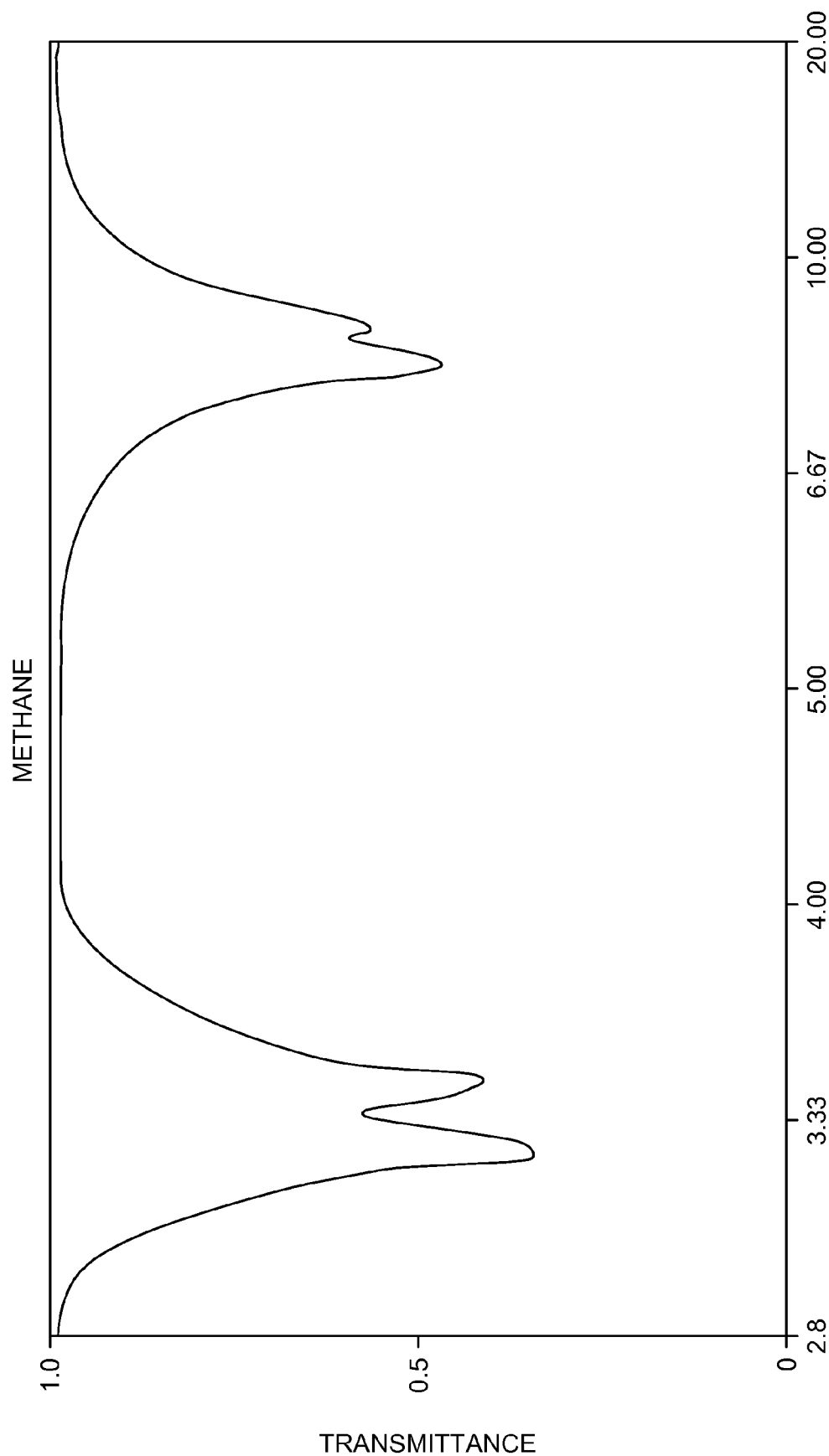
FIG. 4 shows an absorption spectrum.

Before delving into the specifics of the sensor system 316, the specification first touches upon the idea of electromagnetic absorption by chemical molecules, as electromagnetic absorption plays a role with respect to fluid samples and electromagnetic detectors of the various embodiments. In particular, a chemical molecule absorbs particular wavelengths of electromagnetic energy as a function of the structure of the molecule (i.e., discrete excited states of the molecule). That is, when electromagnetic energy (i.e., a photon) is incident upon a molecule, if the energy of the photon matches the energy needed to excite the chemical molecule into one of the molecules discrete excited states, the photon may be absorbed. If the energy of the photon does not match the energy needed to excite the chemical molecule into one of the excited states (e.g., energy of the photon is too high or too low), the photon passes the molecule unimpeded. Consider, as an example, the methane molecule. FIG. 4 shows a graph of methane transmittance (inverse of absorption, and along the Y-axis) of electromagnetic energy against wavelength (the X-axis) of the electromagnetic energy for wavelengths in the infrared region. In particular, electromagnetic energy with wavelengths around 3 microns, and electromagnetic energy with wavelengths around 8 microns, are absorbed by methane. For electromagnetic energy having other wavelengths, for example at 5 microns, the electromagnetic energy passes substantially unimpeded. The graph of FIG. 4 regarding methane is merely illustrative. Each constituent component of a formation fluid has its own absorption spectrum (e.g., water, carbon dioxide, ethane), and by analysis of the absorption spectrum for a fluid some or all the constituent components may be identified.

Figure 5:
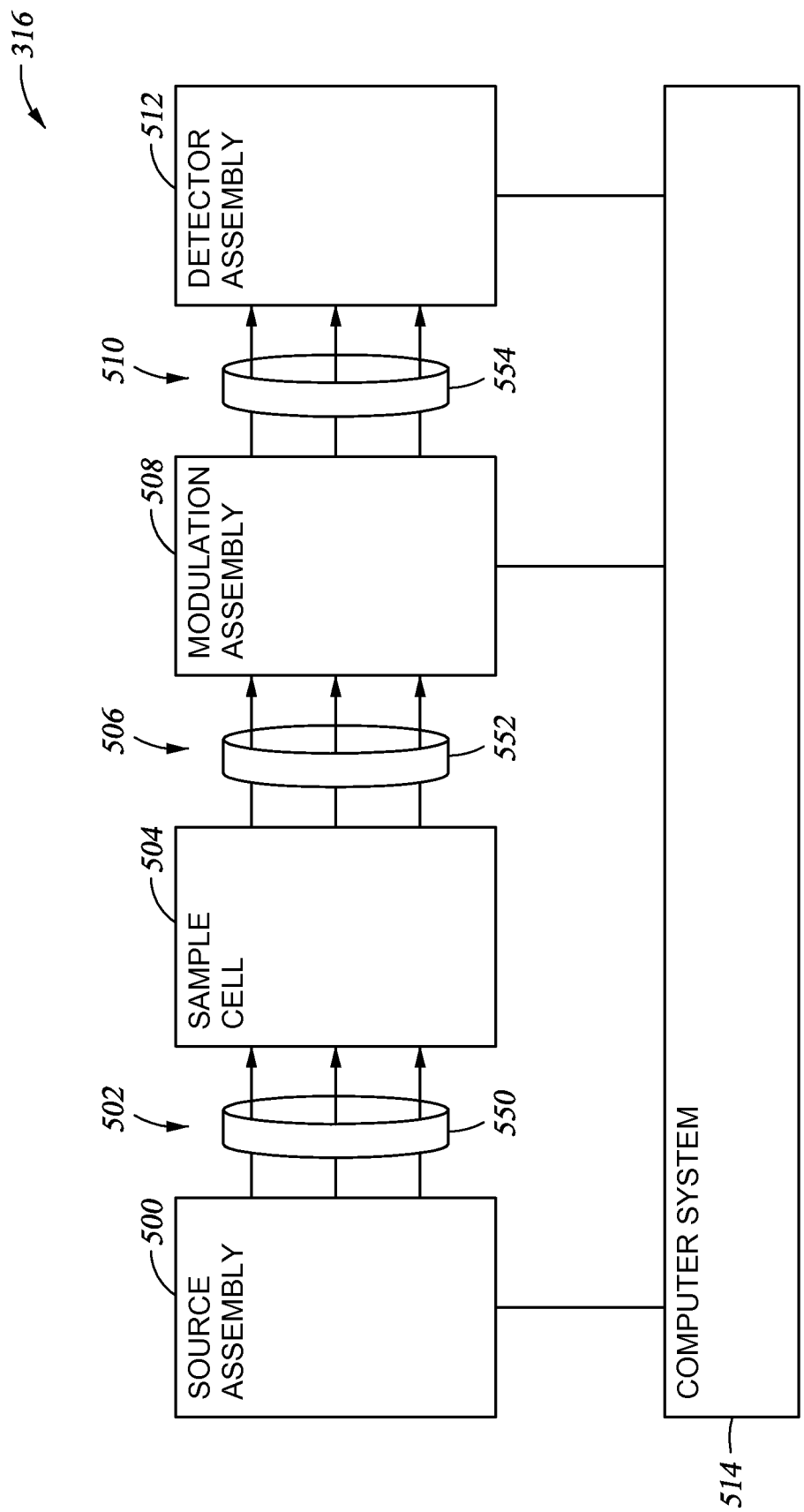
FIG. 5 shows a sensor system in accordance with at least some embodiments.

FIG. 5 shows, in block diagram form, a sensor system 316 in accordance with at least some embodiments. In particular, the sensor system 316 comprises source assembly 500. The source assembly 500 creates electromagnetic energy (i.e., propagating electromagnetic waves), in some cases the electromagnetic energy having wavelengths in the infrared region (e.g., 2.5 micrometers (microns) to 30 microns). The electromagnetic energy created by the source assembly, with the electromagnetic energy illustrated by arrows 502, is optically incident upon a sample cell 504 containing a fluid sample. Chemical molecules of the fluid sample absorb particular wavelengths of electromagnetic energy as a function of the structure of the molecules, and other wavelengths pass unimpeded. The portion of the electromagnetic energy that passes is, in some embodiments, directed to a modulation assembly 508, with the electromagnetic energy illustrated by arrows 506. The modulation assembly 508, when used, modulates the intensity of the electromagnetic energy to match an acoustic resonant frequency of the detector assembly 512. The modulated electromagnetic energy passing through the modulation assembly 508 passes to the detector assembly 512, with the electromagnetic energy illustrated by arrows 510. Electromagnetic energy incident upon the detector assembly creates acoustic energy in the detector assembly at or near the acoustic resonant frequency. By detecting the acoustic energy in the detector assembly 512, the presence or absence of one or more constituent components of the fluid sample in the sample cell may be determined. The overall process is monitored and controlled by a computer system 514, which may control the operation of the source assembly 500 and the modulation assembly 508, and which computer system 514 may also detect the acoustic energy within the detector assembly 512. There are many possible variations of each of the components of FIG. 4, and each component will be discussed in turn, starting with the source assembly 500.

Figure 6:
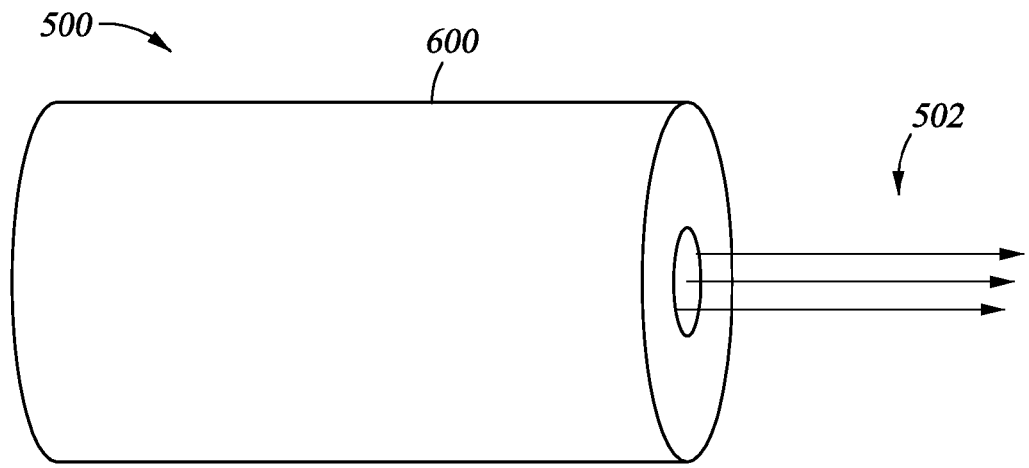
FIG. 6 shows a laser source in accordance with at least some embodiments.

In accordance with various embodiments, the source assembly 500 creates collimated electromagnetic energy with wavelengths in the infrared region. More particularly still, the source assembly creates collimated electromagnetic energy with wavelengths above 1.5 microns, and in particular cases the one or more wavelengths of the electromagnetic energy are between 2.5 microns and 25 microns inclusive. In a particular embodiment, the source assembly is a helium-neon laser producing electromagnetic energy with a wavelength of 3.0 microns. Helium-neon lasers creating electromagnetic energy with a wavelength of 3.0 microns are widely available, such as from Boston Electronics Corporation of Brookline Mass. FIG. 6 shows an illustrative source assembly 500 in the form of a helium-neon laser 600 producing the collimated electromagnetic energy 502.

A laser, by its very nature, produces collimated electromagnetic energy, and thus no further optical equipment may be needed to produce the collimated electromagnetic energy. However, sources of electromagnetic energy other than a laser may be used in the various embodiments. For example, a variety infrared emitters are available (e.g., from Boston Electronics) which use a tungsten filament. Further still, light emitting diodes (LEDs) which produce electromagnetic energy in the infrared region are available (e.g., from Boston Electronics). Yet further still, a quartz-halogen flashlight bulb, in addition to producing electromagnetic energy in the visible spectrum, also produces electromagnetic energy in the infrared region.

Sources of electromagnetic energy in the form of filament-based infrared emitters, infrared LEDs and flashlight bulbs (hereafter "point sources") do not necessarily produced collimated electromagnetic energy; rather, the electromagnetic energy radiates radially outward from the source. Thus, when a point source is used additional mechanisms are implemented to produce the collimated light. In some embodiments, where the physical spacing between the source assembly 500 (FIG. 5) and sample cell 504 (FIG. 5) is not constrained, the collimation of the electromagnetic energy may be accomplished by situating the sample cell 504 a sufficient distance from the point source. However, in cases where the physical distance between the source assembly 500 and sample cell 504 is limited, such as in within a downhole tool, other mechanisms to collimate the electromagnetic energy may be used.

Figure 7:
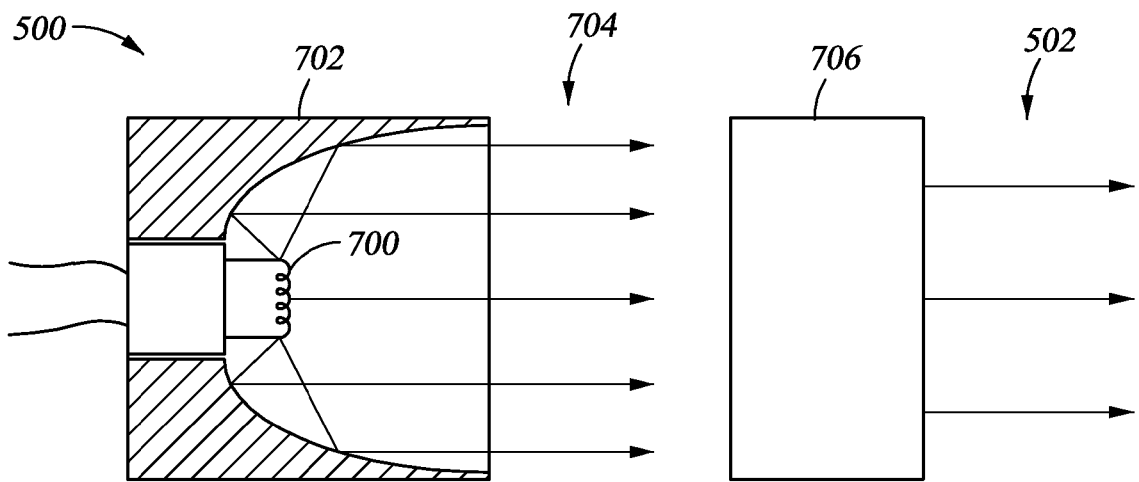
FIG. 7 shows a filament-based source in accordance with at least some embodiments.

FIG. 7 shows an illustrative source assembly 500 in accordance with at least some embodiments. In particular, FIG. 7 shows a point source 700 in the form of a filament-based source, and point source 700 in operational relationship to a parabolic reflector 702 (the parabolic reflector shown in cross-section). Parabolic reflectors are available from a variety of sources, such as Boston Electronics. The point source 700 and parabolic reflector 702 are arranged such that the illustrative filament resides at the focal point for the parabolic reflector. Electromagnetic energy created by the point source 700 radiates radially outward, but in reflecting from the parabolic reflector 702 the electromagnetic energy becomes at least partially collimated, as illustrated by arrows 704.

In accordance with embodiments that use point sources, the point sources may produce electromagnetic energy in the infrared region, but may also produce electromagnetic energy with wavelengths outside desired ranges. Still referring to FIG. 7, in accordance with at least some embodiments the source assembly 500 may further comprise a filter assembly 706 through which the electromagnetic energy is passed. The filter assembly 706 (e.g., an interference filter) blocks the passage of electromagnetic energy of some wavelengths, and allows the passage of electromagnetic energy of other wavelengths. In some cases the filter assembly is a band-pass filter, while in other cases the filter assembly passes wavelengths longer than a predetermined threshold. In some embodiments the electromagnetic energy that leaves the source assembly 500 of FIG. 7, the electromagnetic energy illustrated by arrows 502, has wavelengths above 1.5 microns, and in particular cases the wavelengths of the electromagnetic energy 502 is between 2.5 microns and 25 microns. In situations where the point source 700 produces electromagnetic energy only in a desired range, the filter assembly 706 may be omitted. In yet still other cases, only particular wavelengths may be passed by the filter assembly 706. For example, in a system for detecting methane, a filter assembly may pass only wavelengths to which methane susceptible to absorbing (see, e.g., FIG. 4).

Figure 8:
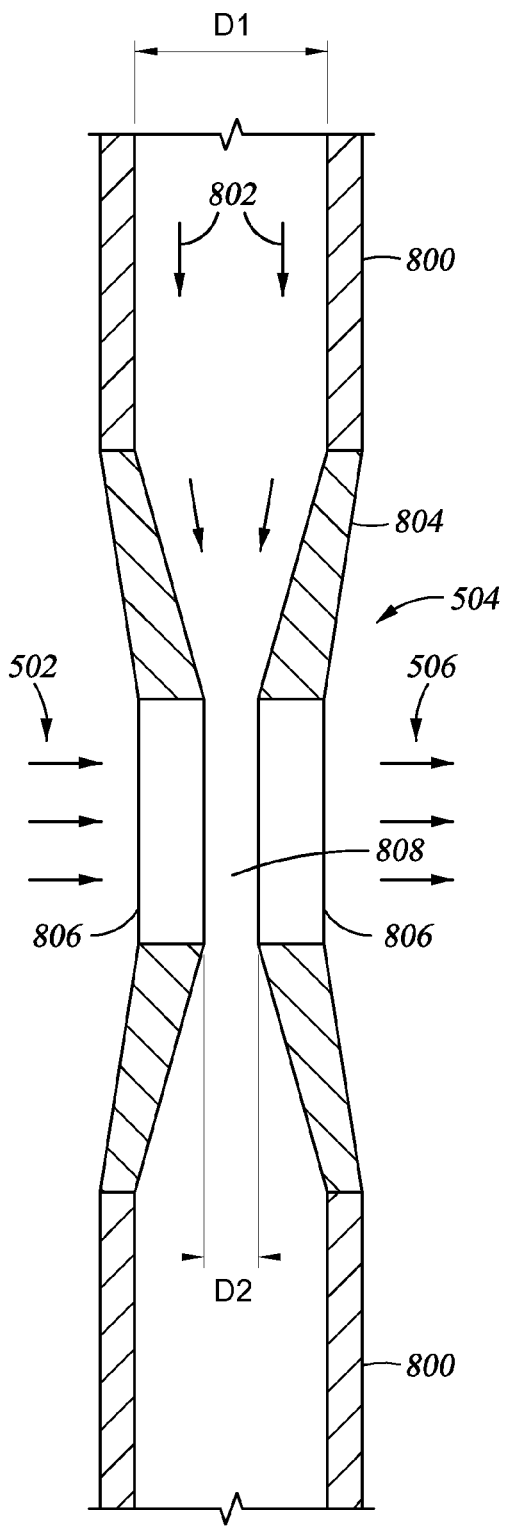
FIG. 8 shows a cross-sectional elevation view of a sample cell in accordance with at least some embodiments.

Returning briefly to FIG. 5, the electromagnetic energy 502 produced by the source assembly 502 is incident upon sample cell 504. In accordance with at least some embodiments, the spectroscopic analysis of the sample fluid is made as the sample fluid flows within or through the sample cell. FIG. 8 shows a cross-sectional view of a sample cell 504 in accordance with at least some embodiments. In particular, the sample cell 504 in these embodiments comprises a fluid conduit 800 having in internal diameter labeled D1 in the figure. For example, the fluid conduit 800 may be a ¼ inch flow line that has a 6 millimeter internal diameter. The sample fluid flows within the fluid conduit 800, the flowing sample fluid illustrated by arrows 802.

The fluid conduit feeds a transition region 804, which transition region 804 directs the sample fluid to flow between two optically aligned windows 806. In at least some embodiments the windows 806 are sapphire, but other material that is substantially optically transparent may be equivalently used. In a particular embodiment, the windows 806 are circular, but the circular nature is not visible in the cross-sectional view of FIG. 8. As illustrated, the collimated electromagnetic energy 502 from the source assembly 500 (FIG. 5) is directed through the optically aligned windows 806. In some cases the source assembly 500 (FIG. 5) and the sample cell 504 are themselves optically aligned, but in other cases the electromagnetic energy 502 may be directed to the sample cell 504 by any suitable structure (e.g., one or more mirrors). The electromagnetic energy 502 interacts with the fluid sample in the region 808 between the windows 806 as the fluid sample flows.

The distance between the windows 806 is selected at the design stage based on the type of sample fluid to be tested, and the distance between the windows 806 is shown as D2 in FIG. 8. For example, when testing formation fluids having substantial heavy liquid hydrocarbon components (i.e., black oil), the distance D2 between the windows 806 may between 1 and 2.5 millimeters inclusive, and in other cases between 1 and 2 millimeters inclusive. However, for other sample fluid to be tested (e.g., substantially optically clear fluids), the designed distance between the windows may be increased.

Still referring to FIG. 8, under Bernoulli's principle, as the cross-sectional area of a fluid flow decreases, there is a corresponding increase in velocity of the fluid flow and decrease in pressure. While in some cases an increase in velocity of the fluid flow between the fluid conduit 800 on the one hand and the fluid flow velocity between the windows 806 on the other hand is not an issue, in other cases the change in velocity may result in undesirable actions (e.g., flashing of liquids to the gas state caused by the effective decrease in pressure). Thus, in accordance with at least some embodiments, the structure that defines the transition region 804, while narrowing in the plane defined by the page upon which FIG. 8 is shown, may widen in directions into and out of the page such that the flow rate of the fluid sample between the windows 806 is substantially the same as the flow rate within the fluid conduit 800. Stated otherwise, in some cases it may be beneficial to design the transition region 804 and windows 806 to ensure proper gap or distance between the windows 806, yet at the same time not causing significantly increased fluid velocity with respect to the balance of the fluid conduit 800.

Figure 9:
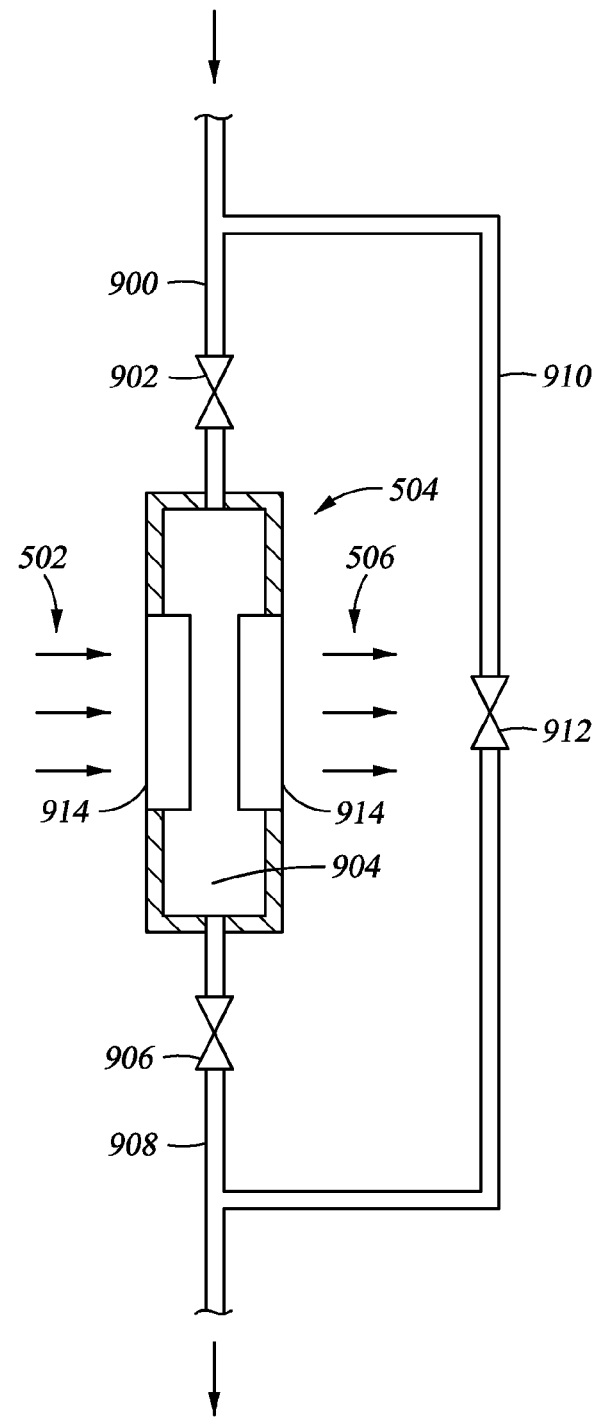
FIG. 9 shows a cross-sectional elevation view of a sample cell in accordance with at least some embodiments.

In yet still other embodiments, the sample cell 504 takes a discrete, non-flowing sample. FIG. 9 shows a cross-sectional view of a sample cell 504 for testing discrete samples, along with associated fluid conduits and valves. In particular, during particular periods of time, sample fluid may flow in fluid conduit 900, through valve 902, through chamber 904, through valve 906 and through fluid conduit 908. During such periods of time, the bypass conduit 910 may be blocked by valve 912. The flow of sample fluid may be caused by any suitable mechanism, such as by pump 310 (FIG. 3). When a sample is to be tested, valves 902 and 906 are closed, thus trapping a discrete sample in the chamber 904. In some embodiments, the valve 912 may open such the fluid may continue to flow through bypass conduit 910. With respect to the discrete fluid sample within the chamber 904, the electromagnetic energy 502 produced by the source assembly 500 (FIG. 5) may be directed through the fluid sample by way of windows 914. Once a sufficient amount of electromagnetic energy 506 has passed through the discrete fluid sample within the chamber 904, valves 902 and 906 may again open, and bypass valve 912 dose, thus flowing fluid through the chamber in preparation for isolating the next discrete fluid sample.

Returning briefly to FIG. 5, depending on the wavelength of the electromagnetic energy 502 and the constituent components of the fluid sample within the sample cell 504, some of the electromagnetic energy may be absorbed by the fluid sample, and thus the electromagnetic energy 506 that propagates through the fluid sample contains information as to one or more constituent components (i.e., the information contained in the reduced presence of particular wavelengths of electromagnetic energy). Thus, in order to determine the presence and/or quantity of constituent components, the electromagnetic energy remaining is detected. In accordance with the various embodiments, the detection of the electromagnetic energy is by way of a photo-acoustic detection system, and in order to use the photo-acoustic detection system the electromagnetic energy 506 is modulated at a frequency of acoustic resonance frequency of the detector (discussed more below). In accordance with at least some embodiments the modulation assembly 508 is placed within the optical path of the electromagnetic energy, and the modulation assembly 508 is responsible for modulating the electromagnetic energy. While the modulation assembly 508 of FIG. 5 is shown in the optical path between the sample cell 504 and the detector assembly, the modulation assembly 508 may be placed at any location in the optical path (e.g., between the source assembly 500 and the sample cell 504, or within the detector assembly between a focusing lens and the acoustic chamber (discussed more below)).

Figure 10:
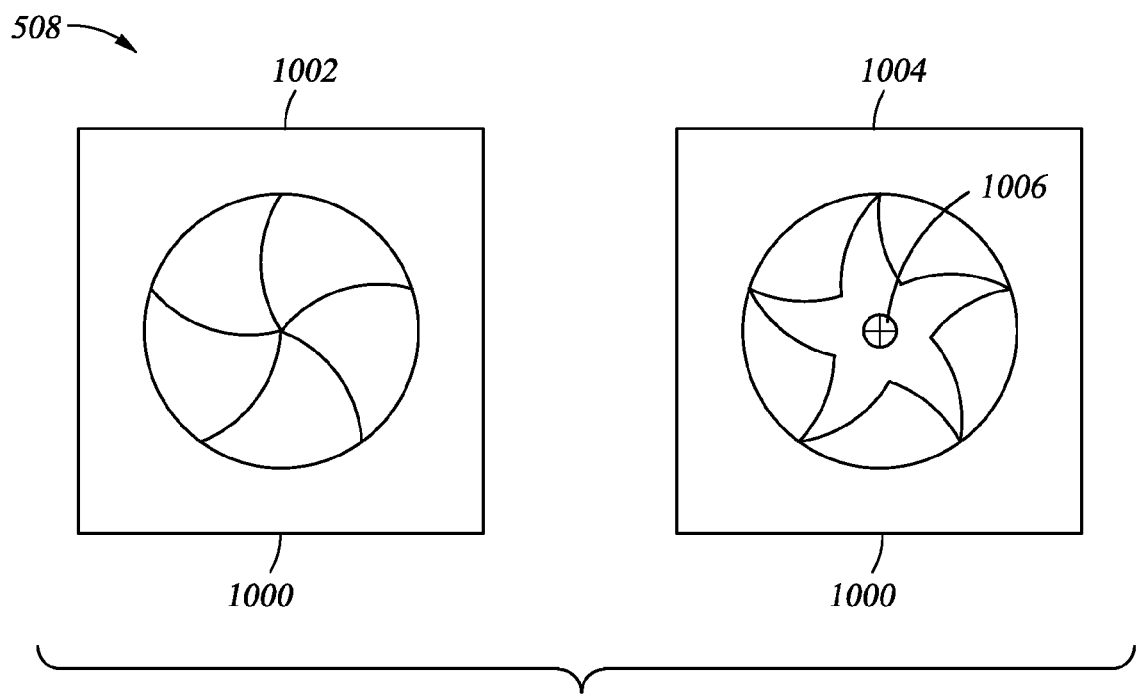
FIG. 10 shows an elevation view of iris-type shutter in accordance with at least some embodiments.

FIG. 10 shows a perspective view of a modulation assembly 508 in accordance with at least some embodiments. In particular, FIG. 10 shows a modulation assembly 508 in the form of an iris-type shutter 1000. The left shutter 1002 is shown in a closed state, while the right shutter 1004 is shown in a partially open state. In accordance with at least some embodiments, the shutter 1000 is placed within the optical path of the electromagnetic energy. When the shutter 1000 is commanded to close (such as by command from the computer system 514 (FIG. 5)), the electromagnetic energy is fully blocked by the shutter 1000. When the shutter 1000 is commanded to open, electromagnetic energy passes through opened iris, as illustrated by the symbol 1006 indicating movement into the page. The frequency at which the shutter is opened and closed (i.e., the frequency at which the electromagnetic energy is blocked and then allowed to propagate) is a design criteria based on the acoustic resonant frequency of the chamber used in the detector assembly 512 (discussed more below). In some cases the frequency is 1000 Hertz or less, and in a particular case is between 400 Hertz or less. Iris-type shutters having the ability to operate at the selected frequencies are available from CVI Melles Griot of Albuquerque, N. Mex.

Figure 11:
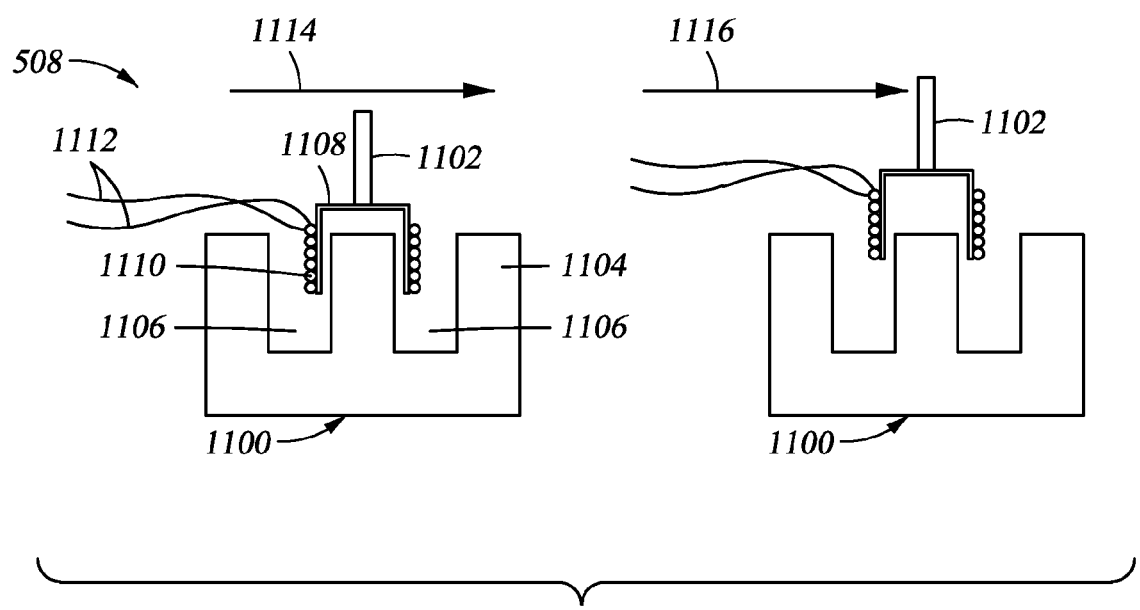
FIG. 11 shows a cross-sectional elevation view of a voice-coil used as a shutter in accordance with at least some embodiments.

FIG. 11 shows a modulation assembly in accordance with alternative embodiments. In particular, FIG. 11 shows a modulation assembly 508 in the form of a voice coil assembly 1100 (shown in cross-section) coupled to a blocking member 1102. The left voice coil assembly 1100 and blocking member 1102 are shown in a retracted state, while the right voice coil assembly 1100 and blocking member 1102 are shown in an extended state. The voice coil assembly comprises a magnet assembly 1104 having an annular groove 1006. Within the annular groove 1006 resides a bobbin 1108 around which several turns of electrical conductor are wound (i.e., windings 1110). Leads 1112 are electrically coupled to the windings, and electrical currents are induced in the windings 1110. Electrical current flow in the windings 1110 creates a magnetic field that interacts with the magnetic field of the magnet assembly 1104. Depending on the direction of current flow forced through the windings, the bobbin 1108, and therefore the blocking assembly 1102, may extend or retract. The voice coil assembly 1100 is placed within the optical path of the electromagnetic energy. When the voice coil assembly 1100 is commanded to retract (such as by command from the computer system 514 (FIG. 5)), the electromagnetic energy propagates unimpeded, as shown by arrow 1114. When the voice coil 1100 is commanded to extend, electromagnetic energy is blocked by the blocking member 1102, as shown by arrow 1116. The frequency at which the electromagnetic energy is blocked and then allowed to propagate is a design criteria based on the acoustic resonant frequency of the chamber used in the detector assembly 512 (discussed more below), but in some cases the frequency is 1000 Hertz or less, and in a particular case 400 Hertz or less.

The modulation assemblies 508 in the form of the shutter assembly 1000 and the voice coil assembly 1100 are merely illustrative of any system that modulates the intensity of the electromagnetic energy. Thus, other modulation techniques may be equivalently used (e.g., turning disk or wheel with apertures therein). The shutter assembly and voice coil assembly modulate the electromagnetic energy in an on-off sense, but complete blocking as part of the modulation need not take place. For example, a shutter assembly that does not fully close, or a voice coil assembly that does not fully block, but where an intensity change is created in the electromagnetic energy is affected, may be equivalently used.

Moreover, in some cases the modulation of the electromagnetic energy may take place at the source assembly 500 (FIG. 5), thus negating the need for a modulation assembly. For example, in the case of the source assembly 500 comprising a laser 600 (FIG. 6), the laser itself may be operated in a pulsed fashion, with the frequency of the pulsations substantially matching the acoustic resonant frequency of the chamber used in the detector assembly 512 (discussed more below). In cases where the source assembly creates the electromagnetic energy by way of a filament-type emitter, the intensity of the electromagnetic energy may be varied at a modulation frequency based on the voltage/current applied to the emitter.

Returning briefly to FIG. 5, the electromagnetic energy 510 that passes through the sample cell 504 and the modulation assembly 508 (if used) is then incident upon the detector assembly 512. The detector assembly 512 in accordance with the various embodiments is a photo-acoustic detector (PAD) device. Unlike related art PAD devices that hold the sample fluid, as shown in FIG. 5 the sample cell 504 (which holds the sample fluid) and the detector assembly 512 are distinct elements. PAD devices are used as detectors in the various embodiments because the operation of such devices are substantially unaffected by expected downhole temperatures, which may reach or exceed 450 Degrees F. At the expected downhole temperatures, other detection devices, particularly semiconductor based devices, have severely degraded performance, if such devices are operable at all. Moreover, and as will be explained more below, the fluid within the PAD device can be tailored to match the constituent components of interest in the sample fluid, thus making the detection highly sensitive to constituent components of interest.

Figure 12:
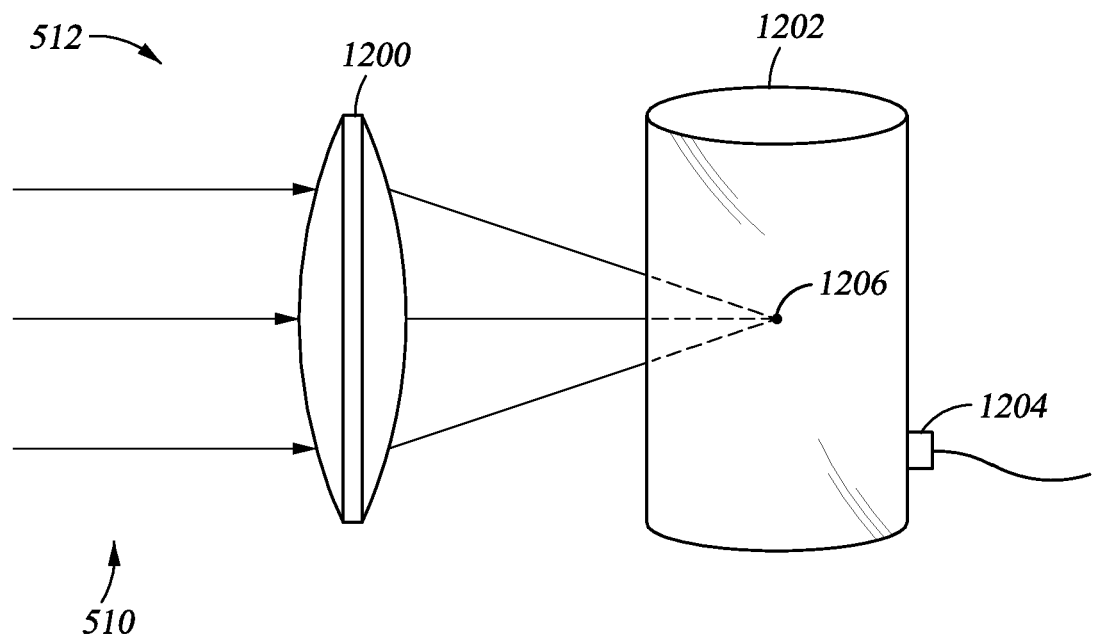
FIG. 12 shows an elevation view of a detector assembly in accordance with at least some embodiments.

FIG. 12 shows a detector assembly 512 in accordance with at least some embodiments. In particular, the illustrative detector assembly of FIG. 12 comprises a focusing lens 1200, an acoustic resonant chamber 1202, and a sensor 1204 coupled to the acoustic resonant chamber 1202. The discussion starts with the acoustic resonant chamber 1202. The resonant chamber 1202 is a structure that defines a sealed internal volume. In order for the electromagnetic energy to enter the resonant chamber 1202, at least a portion of the chamber 1202 is substantially transparent to electromagnetic energy at the wavelengths of interest. In accordance with at least some embodiments, the resonant chamber 1202 is a quartz tube that defines sealed right circular cylinder (as shown); however, other shapes for the resonant chamber may be equivalently used. The internal volume of the resonant chamber 1202 has an acoustic resonant frequency. The precise acoustic resonance frequency is a function of the shape, internal dimensions, and the acoustic velocity of the fluid within the chamber. For example, a confined volume in the form of a cylindrical tube with closed ends such as in FIG. 12 has approximate resonant frequencies as given by the equation:

$$f = \frac{nv}{2L} \qquad (1)$$

where f is a resonant frequency, v is the velocity of sound of the fluid in the tube, n is an odd integer (i.e., 1, 3, 5, . . . ), and L is the length of the tube. Thus, when localized pressure variations are created within the chamber 1202, the pressure variations propagate back and forth within the internal volume. In most cases, the pressure variations cancel; however, when pressure variations are created at a resonant frequency of the chamber, standing pressure waves are created within the internal volume. In some embodiments the resonant frequency is designed and/or selected to be 1000 Hertz or less, and in a particular case 400 Hertz or below.

In some embodiments, the resonant frequency of the chamber 1202 may be controlled and/or changed. For example, the resonance frequency given by equation (1) above is based on the velocity of sound in the chamber. Thus, in order to tune the resonant frequency of the chamber 1202 (e.g., to the chopping frequency of the modulation assembly) the internal pressure or temperature of the chamber may be controlled. For example, the chamber 1202 may have one or more small diameter fingers fluidly coupled to the main chamber 1202. The temperature of the fluid within the finger (or side arm) could be controlled to control temperature and/or pressure within the chamber 1202. Controlling temperature and/or pressure within the chamber 1202 is illustrative of any mechanism to control temperature and/or pressure within the chamber 1202 (e.g., pressure balance the chamber 1202 with baffles).

In accordance with various embodiments, the localized pressure variations leading to the standing pressure waves within the internal volume of the resonant chamber 1202 are created by the electromagnetic energy 510. In particular, in accordance with the various embodiments the resonant chamber 1202 is filled with a detector fluid that has an electromagnetic absorption spectrum that absorbs electromagnetic energy in the range of wavelengths generated by the source assembly 500 (FIG. 5). When electromagnetic energy is incident upon the resonant chamber 1202, the detector fluid within the resonant chamber 1202 absorbs at least a portion of the electromagnetic energy. The absorption results in an increase in molecular activity which manifests itself as a localized increase in pressure. Keeping in mind that electromagnetic energy incident upon the detector assembly 512 has been modulated at the acoustic resonant frequency of the chamber 1202, the periodic and localized pressure increases result in standing acoustic waves in the acoustic chamber 1202. During periods of time when greater intensity of modulated electromagnetic energy is incident upon the resonant chamber 1202, the standing waves within the resonant chamber 1202 have greater amplitude (i.e., the acoustic energy is greater). And during periods of time when the intensity of modulated electromagnetic energy is incident upon the chamber 1202 is reduced, the standing waves within the resonant chamber 1202 have a reduced amplitude (i.e., the acoustic energy is reduced).

Still referring to FIG. 12, while in some cases the electromagnetic energy 510 incident upon the detector assembly 512 may permeate a substantial portion of the resonant chamber 1202, in accordance with at least some embodiments the electromagnetic energy is focused to a focal point within the resonant chamber 1202. To that end, FIG. 12 shows a focusing lens 1200 disposed between the incoming electromagnetic energy 510 and the resonant chamber 1202. The focusing lens 1200 directs the electromagnetic energy to a focal point 1206 within the internal diameter, to help in the creation of pressure waves within the internal volume. As illustrated in FIG. 12, the focal point for the lens 1200 is the center of the internal volume. However, other focal points may be equivalently used, depending on the shape of the resonant chamber and/or the resonance mode.

In accordance with the various embodiments, the amplitude of the acoustic energy in the resonant chamber is sensed as an indication of the presence and/or quantity of one more constituent components in the sample cell 504 (FIG. 5). Sensing the amplitude of the acoustic energy is illustratively shown by sensor 1204. Sensor 1204 could take many forms. In some cases, sensor 1204 is a microphone coupled to the outer surface of the resonant chamber 1202. In other cases, sensor 1204 is a pressure sensor coupled to the resonant chamber 1202 and in fluid communication with the internal volume such that pressure fluctuations associated with the acoustic energy may be sensed. In yet still other embodiments, the sensor 1204 is an accelerometer which senses the acoustic energy as minute vibrations of the resonant chamber 1202. Other sensors may be equivalently used, such as a quartz tuning fork, piezoelectric transducers, voice coil systems, capacitive sensors, electrostatic sensors and optical interference systems (predetermined length of fiber optic wrapped around a portion of the cylinder, and a matching length of fiber optic as a reference, and where minute expansion and contraction of the cylinder causes length differences in the wrapped fiber detected by changes in interference of the light from the two lengths).

Figure 13:
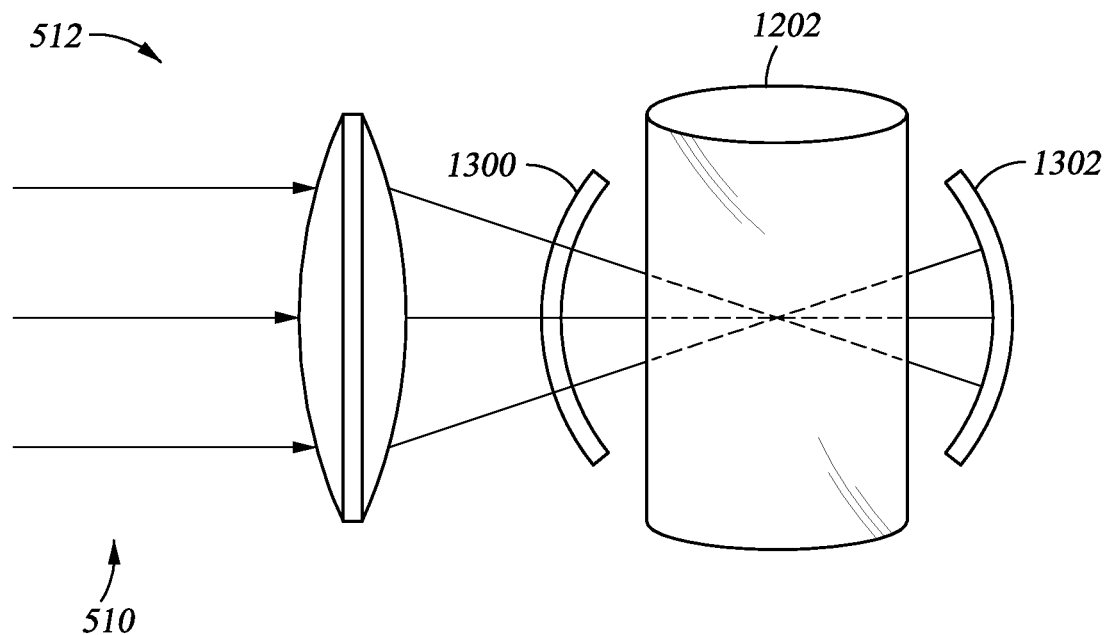
FIG. 13 shows an elevation view of a detector assembly in accordance with at least some embodiments.

Many variations are possible with respect to the detector assembly 512. For example, while the detector assembly 512 of FIG. 12 shows the electromagnetic energy interacting with the detector fluid in a "single pass", in other embodiments the electromagnetic energy may interact with the detector fluid in the resonant chamber 1202 in an optically resonant system such that the electromagnetic energy makes multiple passes through the detector fluid. FIG. 13 shows a detector assembly 512 where the electromagnetic energy 510 is directed between a set of parabolic reflectors 1300 and 1302 such that the electromagnetic energy, once entering the region between the reflectors, oscillates between the reflectors and thus through the detector fluid in the resonant chamber 1202 multiple times. Such optical resonance increases the amount of electromagnetic energy absorbed by the detector fluid, and thus increases the acoustic energy created within the resonant chamber and increases the ability to sense changes in acoustic energy caused by upstream absorption of electromagnetic energy in the sample cell 504. Parabolic reflectors used to create the optical resonance are merely illustrative of any system where the electromagnetic energy is directed through the detector fluid multiple times (e.g., a system of plane mirrors creating a series of optically parallel paths through the detector fluid).

Figure 14A:
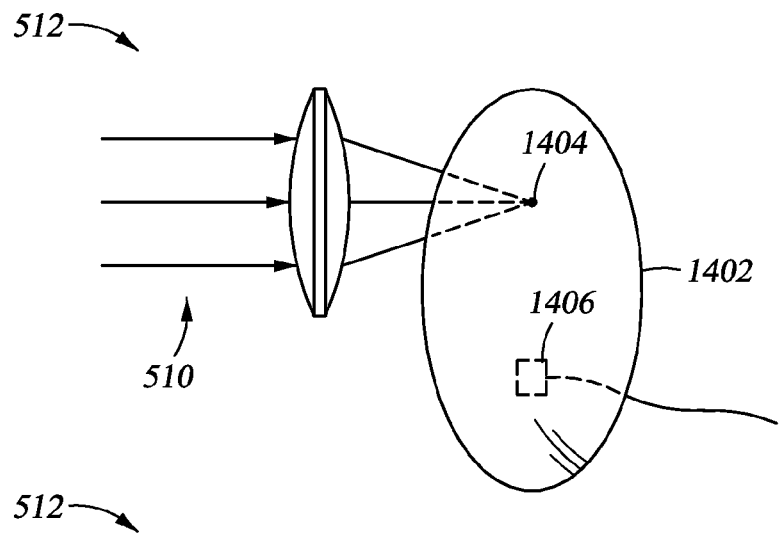
FIG. 14A shows an elevation view of a detector assembly in accordance with at least some embodiments.

Further still, while having a resonant chamber 1202 in the form of a right circular cylinder is convenient to create, and determining the acoustic resonant frequency of the internal volume of the right circular cylinder is a straightforward process, the resonant chamber 1202 is not limited to such a shape. FIG. 14A shows a detector assembly 512 in accordance with alternative embodiments. In particular, FIG. 14A shows the resonant chamber 1402 that defines an elliptical cross-section (i.e., egg shaped). Much like the cylindrical resonant chamber 1202 of FIG. 12, at least a portion of the elliptical resonant chamber 1402 is substantially transparent to electromagnetic energy at the wavelengths of interest. In accordance with at least some embodiments, the resonant chamber 1402 is constructed of quartz. The internal volume of the resonant chamber 1402 has an acoustic resonant frequency. The precise acoustic resonance frequency is a function of the shape, internal dimensions, and the acoustic velocity of the fluid within the chamber.

The resonant chamber 1402 is filled with a detector fluid that has an electromagnetic absorption spectrum that absorbs electromagnetic energy in the range of wavelengths generated by the source assembly 500 (FIG. 5). When electromagnetic energy is incident upon the resonant chamber 1402, the detector fluid within the resonant chamber 1402 absorbs at least a portion of the electromagnetic energy. The absorption results in an increase in molecular activity which manifests itself as a localized increase in pressure leading to standing acoustic waves. As illustrated in FIG. 14A, in accordance with at least some embodiments the electromagnetic energy is focused to a focal point within the resonant chamber 1402, and in particular embodiments the focal point of the electromagnetic energy is a foci 1404 of the elliptical volume. Focusing the electromagnetic energy to the foci may increase sensitivity of the resonant chamber 1402 to the electromagnetic energy, thus making the overall system more sensitive. While FIG. 14A shows only a "single pass" interaction between the electromagnetic energy, acoustic resonance system are also contemplated with the elliptical resonant chamber 1402, but are not shown so as not to unduly complicate the figure.

As with other embodiments, the amplitude of the acoustic energy in the resonant chamber 1404 is sensed as an indication of the presence of one more constituent components in the sample cell 504 (FIG. 5). Sensing the amplitude of the acoustic energy may be way of any suitable device coupled to the exterior surface of the resonant chamber 1404 in the fashion discussed above with the respect to resonant chamber 1202 (FIG. 12); however, in a particular embodiment, and as illustrated in FIG. 14A, sensor 1406 may be placed within the internal volume, and more particularly at the foci of the elliptical volume opposite the location where the electromagnetic energy is focused. Placing the sensor 1406 at the foci may increase the sensitivity of the sensor to acoustic energy within the elliptical internal volume, thus making the overall system more sensitive.

Figure 14B:
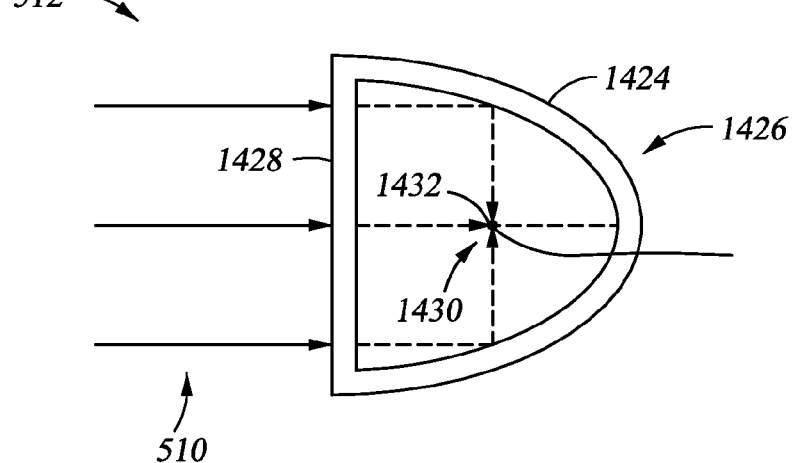
FIG. 14$b$ shows a cross-sectional elevation view of a detector assembly in accordance with at least some embodiments.

FIG. 14B shows a detector assembly 512 in accordance with yet still further alternative embodiments. In particular, FIG. 14B shows a cross-sectional elevation view of the resonant chamber 1424 that defines a parabolic cross-section (portion 1426) with a flat surface 1428 sealing the portion 1426. Much like the cylindrical resonant chamber 1202 of FIG. 12, at least a portion of the resonant chamber 1424 is substantially transparent to electromagnetic energy at the wavelengths of interest, and in some embodiments at least the sealing portion 1428 is substantially transparent. In accordance with at least some embodiments, the resonant chamber 1424 is constructed of quartz. The internal volume of the resonant chamber 1424 has an acoustic resonant frequency. The precise acoustic resonance frequency is a function of the shape, internal dimensions, and the acoustic velocity of the fluid within the chamber.

The resonant chamber 1424 is filled with a detector fluid that has an electromagnetic absorption spectrum that absorbs electromagnetic energy in the range of wavelengths generated by the source assembly 500 (FIG. 5). The detector fluid within the resonant chamber 1424 absorbs at least a portion of the electromagnetic energy. The absorption results in an increase in molecular activity which manifests itself as a localized increase in pressure leading to standing acoustic waves. As illustrated in FIG. 14B, in accordance with at least some embodiments the electromagnetic energy is focused to a focal point 1430 within the resonant chamber 1424 by the portion 1426 itself. In other cases, the electromagnetic energy may be focused by an external focusing lens. Focusing the electromagnetic energy to the foci may increase sensitivity of the resonant chamber 1424 to the electromagnetic energy, thus making the overall system more sensitive.

As with other embodiments, the amplitude of the acoustic energy in the resonant chamber 1424 is sensed as an indication of the presence of one more constituent components in the sample cell 504 (FIG. 5). Sensing the amplitude of the acoustic energy may be way of any suitable device coupled to the exterior surface of the resonant chamber 1404 in the fashion discussed above with the respect to resonant chamber 1202 (FIG. 12); however, in a particular embodiment, and as illustrated in FIG. 14B, sensor 1432 may be placed within the internal volume, and more particularly at the focal point 1430 of the parabolic portion 1426. Placing the sensor 1406 at the focal point may increase the sensitivity of the sensor to acoustic energy within the elliptical internal volume, thus making the overall system more sensitive.

Figure 15:
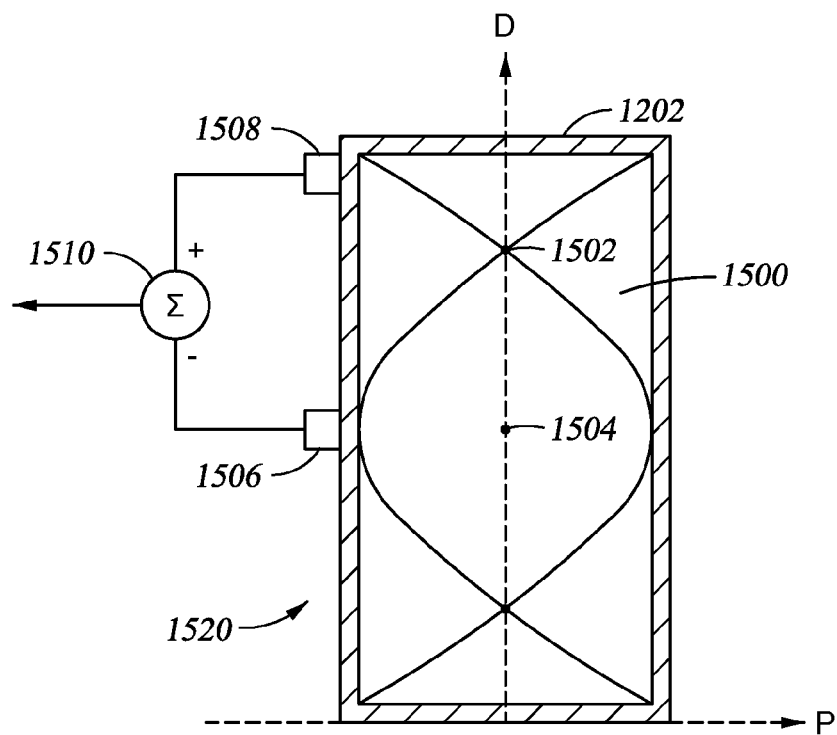
FIG. 15 shows a cross-sectional elevation view of a resonant chamber in accordance with at least some embodiments.

In at least some embodiments the sensor assembly 316 will be used in a tool within a bottomhole assembly 102 of a drilling operation. For that reason, the sensor assembly 316 may experience or be subject to vibration from any of variety of downhole sources. The vibration may, in some cases, manifest itself as noise in the detection of the acoustic energy within the resonant chamber of the detector assembly 512. In accordance with at least some embodiments, the acoustic energy of the resonant chamber is sensed in such a way as to reduce the effect of vibration through the use of differential detection. FIG. 15 show cross-sectional view of an illustrative right circular cylinder resonant chamber 1202. Superimposed on the resonant chamber 1202 is a coordinate system (in dashed lines) comprising distance D vertically, and pressure P horizontally. Shown plotted within the internal volume 1500 are pressure waveforms as a function of distance D within the internal volume 1500 for the n=1 fundamental standing acoustic wave. For example, if one could "see" the pressure within the internal volume 1500 at point 1502, for a standing wave within the internal volume 1500 no pressure changes would be seen at point 1502 (i.e., a node) (pressure waves propagate past point 1502, but the superposition of the oppositely traveling waves results in a node) Likewise, if one could "see" the pressure within the internal volume 1500 at point 1504, for a standing wave within the internal volume 1500 pressure swings from positive to negative would be seen at point 1504 (i.e., an antinode).

Thus, in some embodiments the acoustic energy within the internal volume 1500 is sensed differentially. That is, two sensors 1506 and 1508 are used as a differential sensor pair. One sensor 1506 is placed at a first antinode, and the second sensor 1508 is placed a second antinode (of opposite phase relationship), and the sensed parameter (e.g., pressure, acceleration) is determined as the difference between the readings, as shown by the function block 1510. The differential detection system is less sensitive to vibration because vibration tends to affect each sensor 1506, 1508 in the same phase relationship. For example, consider a vibratory shock as illustrated by line 1520. Both sensors 1506 and 1508 will "feel" the shock in the same direction; however, because the final signal is the mathematical subtraction of the two readings, the vibration is effectively removed from final reading. A rotational vibratory shock (with the center of rotation between the sensors 1506, 1508) may not be removed by the differential system; however, the various embodiments include systems where the additional sensor sets, distributed about the resonant chamber, are used, where at least one set of sensors can sense acoustic energy within resonant chamber as a differential pair that is overall less sensitive to vibratory motion.

Returning to FIG. 5, a sensor system 316 in accordance with the various embodiments derives increased sensitivity by a relationship between the one or more constituent components in the sample cell and the detector fluid in the resonant chamber of the detector assembly 512. In particular, the detector fluid in the resonant chamber of the detector assembly 512 is selected to be related, in an electromagnetic energy absorption sense, to the one more constituent components. More precisely, the detector fluid in the resonant chamber of the detector assembly 512 has an absorption spectrum (e.g., FIG. 4) that overlaps with the one or more constituent components. In some embodiments the detector fluid and the constituent component is the same.

Consider, as an example, that the sensor system 316 is used to detect the presence and/or quantity of methane in the fluid sample in the sample cell 504. Further consider that the detector fluid in the resonant chamber of the detector assembly comprises methane. During periods of time when the fluid sample in the sample cell 504 contains low amounts of methane, the infrared wavelengths of the electromagnetic energy 506 that passes through the sample cell 504 will comprises greater intensity of wavelengths that are absorbed by methane. The electromagnetic energy 506, 510 impinging upon the resonant chamber of the detector assembly 512 will thus comprise greater intensity of such wavelengths. It follows that illustrative methane in the resonant chamber will absorb a more energy, thus producing acoustic resonance with a particular amplitude.

During periods of time when the fluid sample in the sample cell 504 contains high amounts of methane, the infrared wavelengths of the electromagnetic energy 506 that passes through the sample cell 504 will comprises lesser intensity of wavelengths that are absorbed by methane, because more of those wavelengths are absorbed by the methane in the fluid sample. The electromagnetic energy 506, 510 impinging upon the resonant chamber of the detector assembly 512 will thus comprise a lesser intensity of such wavelengths. The methane in the resonant chamber will still absorb electromagnetic energy, but because less of such energy in the wavelengths that is absorbed by methane will be present, the acoustic resonance produced will have lower amplitude than the case of no methane in the fluid sample. Wavelengths of the electromagnetic energy that are not substantially absorbed by the detector fluid thus do not contribute to the creation or amplitude of acoustic energy in the resonant chamber. Thus, the detector assembly 512 can not only distinguish the presence of a particular constituent component in the fluid sample (based on a reduction in the amplitude of acoustic energy in the resonant chamber), but the detector assembly 512 can also quantify the amount of constituent component (based on the magnitude of the reduction in the amplitude of the acoustic energy).

Detecting a constituent component being methane by use of methane in the resonant chamber is merely illustrative. Any of a variety of constituent components may be of interest, and likewise any of a variety of detector fluids may be used. For example, a non-limited list of constituent components for which the presence and/or quantity may be tested comprise any constituent of a hydrocarbons within a reservoir, such as: water, carbon dioxide, methane, ethane, propane, butane, pentane, octane, and hydrogen sulfide. Moreover, the constituent components for which tests are run may provide, directly or indirectly, other quality or economic viability information, such as the relative presence of saturates, aromatics, resins, and asphaltenes in the fluid sample.

Figure 16:
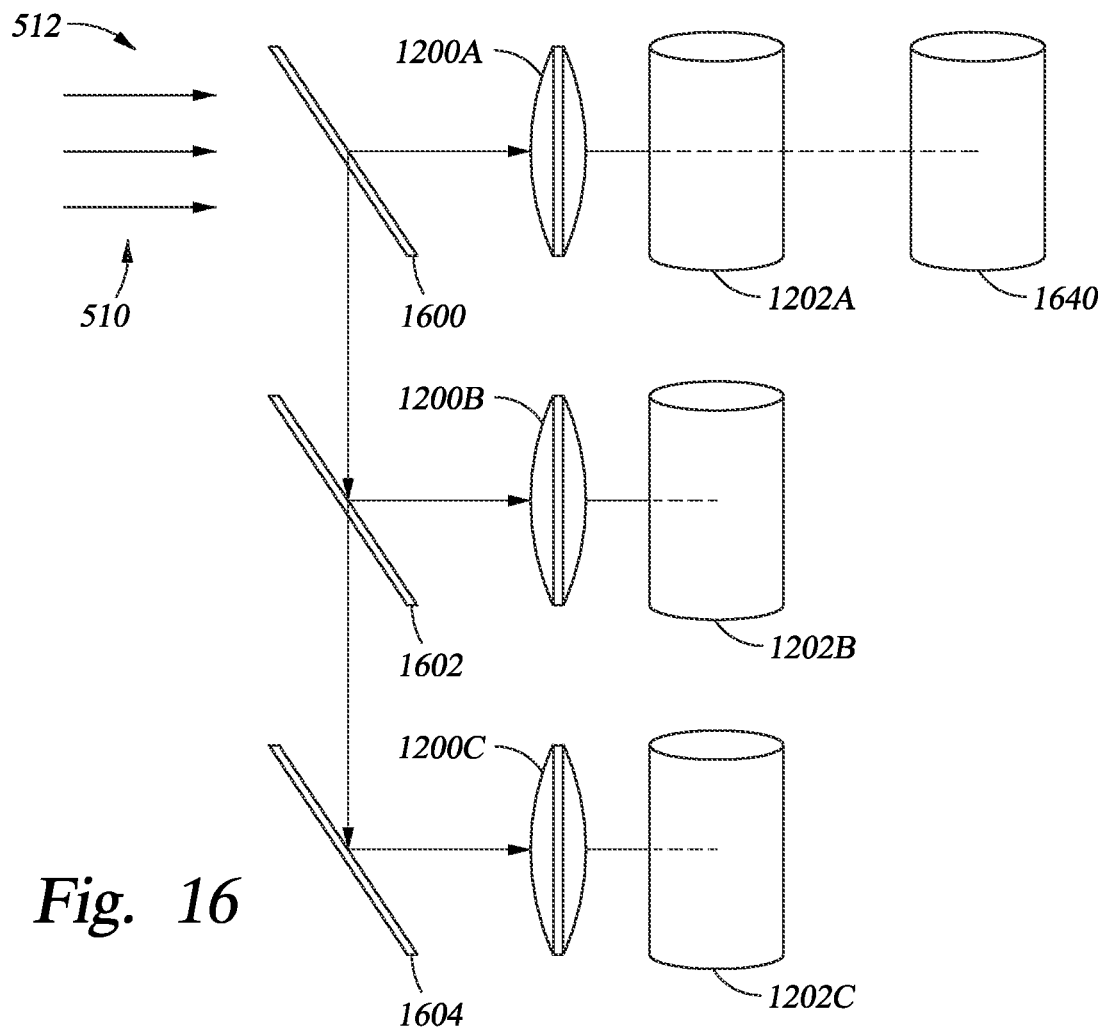
FIG. 16 shows an elevation view of a detector assembly in accordance with at least some embodiments.

In some cases, where multiple constituent components of the fluid sample are of interest, multiple resonant chambers may be used. FIG. 16 shows a detector assembly 512 comprising a plurality of resonant chambers. In particular, the detector assembly 512 of FIG. 16 has three resonant chambers 1202 in parallel (and a fourth resonant chamber 1640 discussed more below). Each resonant chamber likewise has its own lens 1200. The electromagnetic energy 510 that enters the detector assembly 512 encounters a beam splitter 1600. The portion of the electromagnetic energy that passes through the beam splitter 1600 impinges upon resonant chamber 1202A through lens 1200A. The portion of the electromagnetic energy that is reflected by the beam splitter 1600 is directed to a second beam splitter 1602. The portion of the electromagnetic energy that passes through the beam splitter 1602 impinges upon resonant chamber 1202B through lens 1200B. The portion of the electromagnetic energy that is reflected by the beam splitter 1602 is directed to mirror 1604, which directed the electromagnetic energy to the resonant chamber 1202C through lens 1200C.

Each of the chambers 1202 in FIG. 16 may have a different detector fluid. For example, resonant chamber 1202A could contain carbon dioxide, resonant chamber 1202B could contain methane, and resonant chamber 1202C could contain sulfur dioxide. Thus, resonant chamber 1202A is particularly sensitive to carbon dioxide, resonant chamber 1202B is particularly sensitive to methane, and resonant chamber 1202C is particularly sensitive to sulfur dioxide. However, it is noted that the illustrative sulfur dioxide may be a "proxy" fluid for other compounds, such as hydrogen sulfide. That is, the detector fluid need not be the same as the constituent component in some embodiments; rather, the detector fluid can merely have an absorption spectrum that overlaps with the absorption spectrum of the constituent component.

Still referring to FIG. 16, embodiments with multiple detector assemblies are not limited to resonant chambers in parallel. In particular, in some embodiments the resonant chambers may be placed in series such that electromagnetic energy that passes through one chamber may then be incident on another resonant chamber. In FIG. 16, electromagnetic energy that passes through resonant chamber 1202A may then by directed to a second resonant chamber 1640. Thus, the first resonant chamber 1202A may be configured for detection with respect to a first constituent component (or first grouping of constituent components), and the second resonant chamber 1640 may be configured for a detection with respect to a second constituent component (or second grouping of constituent components).

So as not to unduly complicate gaining an understanding of the various embodiments, the illustrative detector fluids discussed to this point have been a single component (e.g., methane, carbon dioxide). However, in accordance other embodiments, the detector fluid within a particular resonant chamber may be a mixture of fluids. For example, in some embodiments where the presence of methane, ethane and related compounds in the fluid sample are of interest, the detector fluid may contain methane and ethane. Not only will the methane and ethane be responsive to methane and ethane in the fluid sample, but methane, ethane, or the combination may be a proxy for other higher order hydrocarbons in the fluid sample. As another example, in cases where constituent components of carbon dioxide and water are of interest in the fluid sample, a resonant chamber may contain water vapor and carbon dioxide.

The detector assembly 512 in accordance with the various embodiments is thus "tuned" to one or more constituent components based on the selection of the detector fluid. It is the absorption by the detector fluid, with the detector fluid having an electromagnetic absorption spectrum that is the same or that overlaps with the one or more constituent components, that provides increased sensitivity. By contrast, some related-art devices use solid black-body absorbers within the acoustic resonant chamber (e.g., carbon black), with the internal solid absorber sometimes referred to as a diaphragm. The energy absorbed by the diaphragm is converted to heat, which then creates localized temperature increases and corresponding pressure increases. In such systems the black-body absorbers within the chamber absorb substantially all incident electromagnetic energy, regardless of wavelength. The fluid within the chamber contributes little, if any, absorption. Moreover, in absorbing substantially all incident electromagnetic energy, the sensitivity to changes in intensity of electromagnetic energy in particular wavelength is masked by the broadband absorption. Thus, detector assemblies 512 in accordance with the various embodiments not only rely on direct absorption of the electromagnetic energy by the detector fluid, but also detector assemblies do not use solid black-body electromagnetic energy absorption devices within the resonant chambers. Substantially all the electromagnetic radiation is absorbed by the detector fluid.

The various embodiments discussed to this point have assumed that the electromagnetic energy propagates from place to place unconstrained (i.e., in air), with directivity based mirrors and line of sight. However, in accordance with yet still other embodiments the electromagnetic energy may propagate from place to place within optical fibers. Returning again to FIG. 5, in accordance with at least some embodiments the various stages of the electromagnetic energy 502, 506, 510 may be directed through respective optical fibers. For example, an optical fiber 550 (or bundle of optical fibers) may transfer the electromagnetic energy from the source assembly 500 to the sample cell 504. Likewise, an optical fiber 552 (or bundle of optical fibers) may transfer the electromagnetic energy from the sample cell 504 to the modulation assembly 508. Further, an optical fiber 554 (or bundle of optical fibers) may transfer the electromagnetic energy from the modulation assembly 508 to the detector assembly 512.

Figure 17:
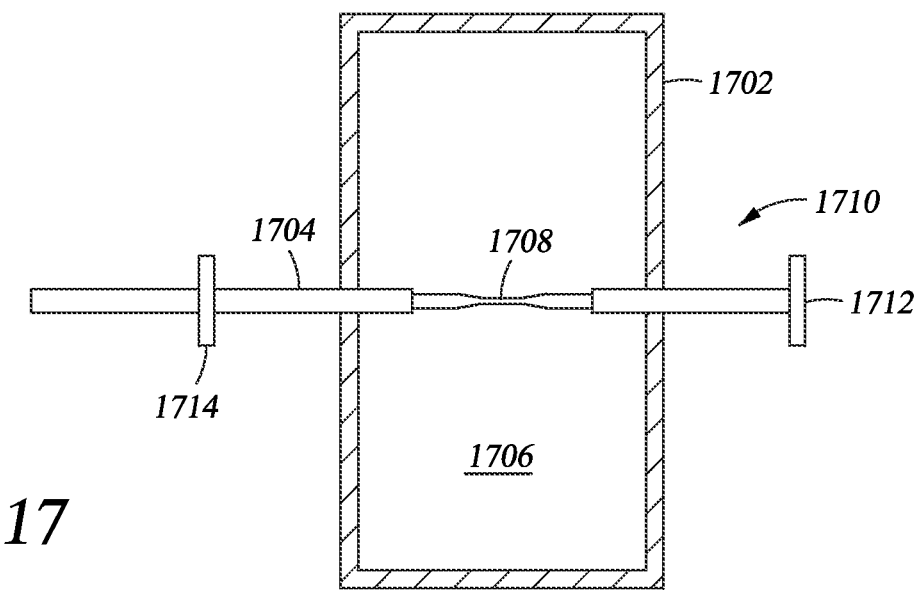
FIG. 17 shows a cross-sectional elevation view of a resonant chamber using fiber optics in accordance with at least some embodiments.

In accordance with yet still further embodiments, optical fiber may be the mechanism by which the electromagnetic energy is conveyed into the resonant chamber of the detector assembly 512, and by which interaction between the fluid within the resonant chamber and the electromagnetic energy is facilitated. In particular, FIG. 17 shows a cross-sectional elevation view of a resonant chamber 1702 in accordance with at least some embodiments. In the particular embodiment, the electromagnetic energy that passes through the sample cell 504 (FIG. 5) is conveyed to the resonant chamber 1702 by optical fiber 1704 (the size of which is greatly exaggerated for purposes of discussion). The optical fiber passes into the internal volume 1706 of the chamber 1702. In accordance with these embodiments, the optical fiber 1704 within the internal volume 1706 has a subwavelength-diameter taper portion 1708 from which the cladding has been removed. That is, the exterior protective coating has been removed in portion 1708, and the diameter of optical fiber made smaller (such as by pulling the fiber while heating the portion to be tapered). The diameter of the taper portion 1708 is less than the wavelength of electromagnetic energy of interest, and in some embodiments the diameter of the taper portion 1708 is 50 to 150 nanometers (0.050 to 0.15 microns). Electromagnetic energy flowing through taper portion 1708 creates a highly concentrated optical field at the taper portion 1708. Moreover, given the relationship between the wavelength of the electromagnetic energy and the diameter of the optical fiber at the taper portion 1708, the electromagnetic energy tends to propagate outside the optical fiber, yet is still directed by the optical fiber. Such propagation mode may be referred to as an evanescent field.

In accordance with the embodiments of FIG. 17, the electromagnetic energy interacts with the fluid inside the chamber 1702 at the taper portion 1708. That is, fluid inside the chamber 1702 absorbs particular wavelengths (as discussed above) which creates localized areas of increased pressure that in turn create standing waves based on the modulation frequency of the electromagnetic energy. As illustrated, the taper portion 1708 may reside at a node of the chamber 1702. Though not specifically shown, when the optical fiber is used with chambers having a focal point (e.g., sealed parabolic chamber) or foci (e.g., elliptical chamber), the taper portion 1708 may reside at the focal point or foci.

In some embodiments, the optical fiber 1704 may terminate at the taper portion 1708, but as shown the optical fiber continues past the taper portion 1708 (as shown by portion 1710). When the optical fiber terminates at the taper portion 1708, the electromagnetic energy can be though of as making a single "pass" through the fluid in the chamber 1702. However, in other embodiments using optical fiber an optically resonant structure may be created using a mirror 1712 on the distal end of the optical fiber, along with a mirror 1714 that allows electromagnetic energy to pass from the sample cell to the chamber 1702 substantially unimpeded (electromagnetic energy moving left to the right across the mirror 1714), but which reflects electromagnetic energy propagating back toward the mirror 1714 (electromagnetic energy moving right to left in the figure). Thus, once electromagnetic energy enters the portion of the optical fiber between the mirrors 1714 and 1710, the energy propagates back and forth through the taper portion 1708 until the energy dissipates (e.g., in losses within the fiber) or is absorbed by the fluid in the chamber 1706.

Still referring to FIG. 17, the mirrors 1714 and 1710 are merely illustrative of any system which forces the electromagnetic energy constrained to (or around) the optical fiber to pass the taper portion 1708 multiple times. Other systems may be equivalently used. For example, a loop of optical fiber may be created, where the loop passes through the internal volume 1706, and where a portion of the loop has the taper portion 1708. Electromagnetic energy may be coupled to the loop from an optical fiber carrying the electromagnetic energy that passes through the sample cell (e.g., the coupling by an evanescent coupler). Thus, once electromagnetic energy is coupled to the loop, the energy propagates around the loop until the energy is absorbed by the fluid or dissipates in the losses of the optical fiber loop.

Figure 18:
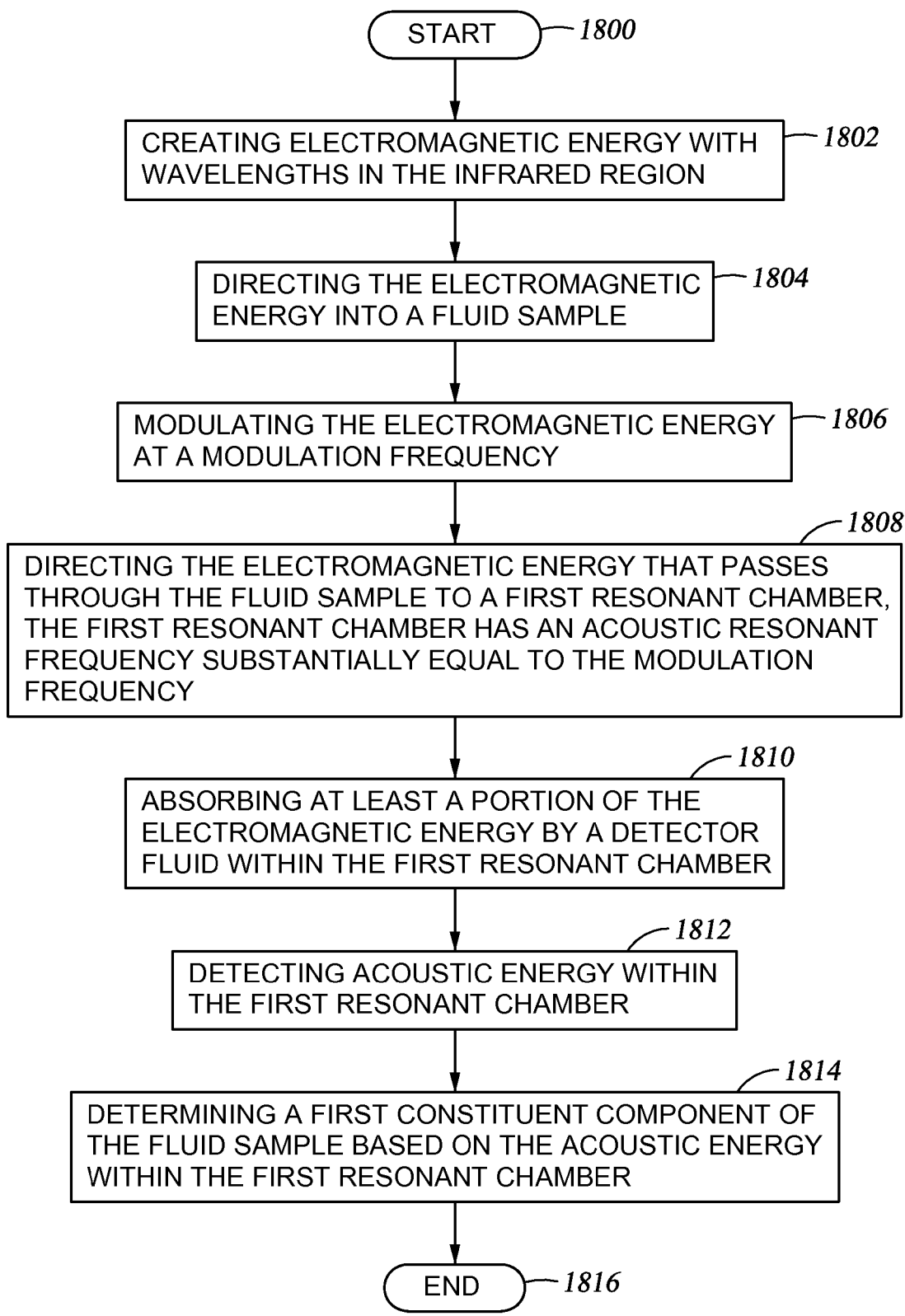
FIG. 18 shows a method in accordance with at least some embodiments.

FIG. 18 shows a method in accordance with at least some embodiments. In particular, the method starts (block 1800) and proceeds to: creating electromagnetic energy with a wavelength in the infrared region (block 1802); directing the electromagnetic energy into a fluid sample (block 1804);

modulating the electromagnetic energy at a modulation frequency (block 1806); directing the electromagnetic energy that passes through the fluid sample to a first resonant chamber, the first resonant chamber has an acoustic resonant frequency substantially equal to the modulation frequency (block 1808); absorbing at least a portion of the electromagnetic energy by a detector fluid within the first resonant chamber (block 1810); detecting acoustic energy within the first resonant chamber (block 1812); and determining a first constituent component of the fluid sample based on the acoustic energy within the first resonant chamber (block 1814). Thereafter, the method ends (block 1816).

Figure 19:
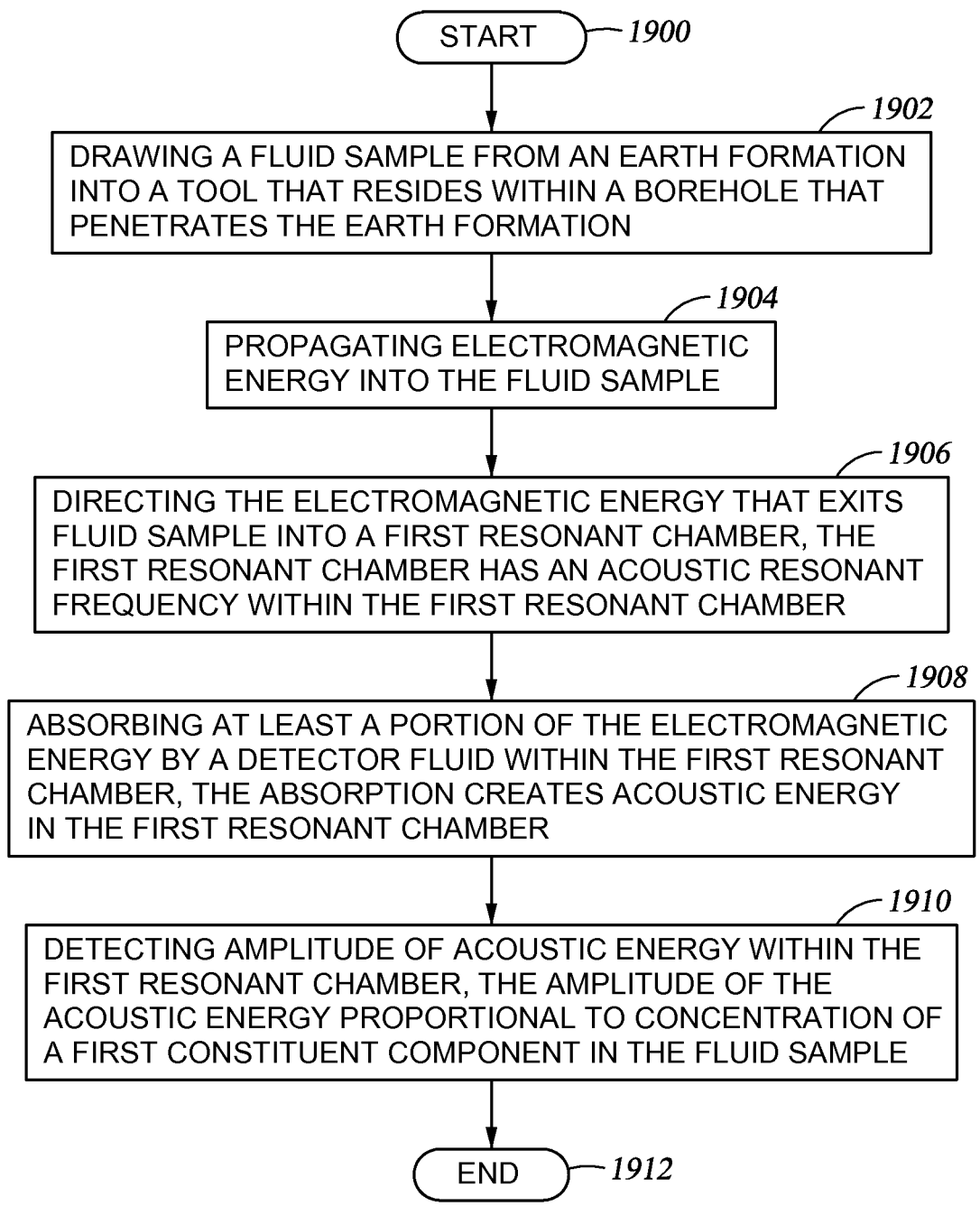
FIG. 19 shows a method in accordance with at least some embodiments.

FIG. 19 shows a method in accordance with at least some embodiments. In particular, the method starts (block 1900) and proceed to: drawing a fluid sample from an earth formation into a tool that resides within a borehole that penetrates the earth formation (block 1902); propagating electromagnetic energy into the fluid sample (block 1904); directing the electromagnetic energy that exits fluid sample into a first resonant chamber, the first resonant chamber has an acoustic resonant frequency within the first resonant chamber (block 1906); absorbing at least a portion of the electromagnetic energy by a detector fluid within the first resonant chamber, the absorption creates acoustic energy in the first resonant chamber (block 1908); and detecting amplitude of acoustic energy within the first resonant chamber, the amplitude of the acoustic energy proportional to concentration of a first constituent component in the fluid sample (block 1910). Thereafter, the method ends (block 1912).

The above discussion is meant to be illustrative of the principles and various embodiments of the present invention. Numerous variations and modifications will become apparent to those skilled in the art once the above disclosure is fully appreciated. Moreover, while the various embodiments shows directing the electromagnetic energy by way of mirrors and alignment, in other embodiments the electromagnetic energy may be optically controlled and directed through any suitable mechanism, such as optical pipes. It is intended that the following claims be interpreted to embrace all such variations and modifications.

What is claimed is:

1. A method comprising:
   creating electromagnetic energy with wavelengths in the infrared region;
   directing the electromagnetic energy into a fluid sample;
   modulating the electromagnetic energy at a modulation frequency;
   directing the electromagnetic energy that passes through the fluid sample to a first resonant chamber, the first resonant chamber has an acoustic resonant frequency substantially equal to the modulation frequency;
   absorbing at least a portion of the electromagnetic energy by a detector fluid within the first resonant chamber;
   detecting acoustic energy within the first resonant chamber; and
   determining a first constituent component of the fluid sample based on the acoustic energy within the first resonant chamber.

2. The method of claim 1 wherein directing the electromagnetic energy through the fluid sample further comprises directing electromagnetic energy having wavelength between and including 1.5 micrometers (microns) and 25 microns.

3. The method of claim 1, wherein creating electromagnetic energy further comprises:
   creating electromagnetic energy in both the visible region and infrared region; and then
   filtering the electromagnetic energy such that only electromagnetic energy in the infrared region remains.

4. The method of claim 1 wherein directing the electromagnetic energy into the fluid sample further comprises directing the electromagnetic energy into the fluid sample flowing through a sample region.

5. The method of claim 1 wherein directing the electromagnetic energy into a fluid sample further comprises directing the electromagnetic energy into a sample chamber holding a discrete volume that is stationary relative to the sample chamber.

6. The method of claim 1 wherein modulating further comprises cyclically blocking propagation of the electromagnetic energy and allowing the propagation of the electromagnetic energy, the blocking and allowing repeat at the modulation frequency.

7. The method of claim 1 wherein absorbing at least a portion of the electromagnetic energy by the detector fluid further comprises absorbing by the detector fluid, the detector fluid having an electromagnetic absorption spectrum that overlaps with an electromagnetic absorption spectrum of the first constituent component.

8. The method of claim 7 wherein absorbing further comprises absorbing by the detector fluid being, at least in part, the same as the first constituent component.

9. The method of claim 1 wherein detecting acoustic energy further comprises detecting by a sensor located at a node of standing waves within the first resonant chamber.

10. The method of claim 1 wherein detecting acoustic energy further comprises differentially detecting by at least two sensors, each sensor located at an anti-node of standing waves within the first resonant chamber.

11. The method of claim 1 further comprising:
    prior to the directing, splitting the electromagnetic energy that passes through the fluid sample into a first beam and a second beam; and then
    directing the first beam of electromagnetic energy to the first resonant chamber;
    directing the second beam of electromagnetic energy to a second resonant chamber, the second resonant chamber has an acoustic resonant frequency;
    absorbing at least a portion of the second beam of electromagnetic energy by a fluid within the second resonant chamber;
    detecting acoustic energy within the second resonant chamber; and
    determining a second constituent component of the fluid sample based on the acoustic energy within the second resonant chamber.

12. The method of claim 1 further comprising:
    directing electromagnetic energy that passes through the first resonant chamber to a second resonant chamber, the second resonant chamber has an acoustic resonant frequency;
    absorbing at least a portion of the second beam of electromagnetic energy by a fluid within the second resonant chamber;
    detecting acoustic energy within the second resonant chamber; and
    determining a second constituent component of the fluid sample based on the acoustic energy within the second resonant chamber.

13. The method of claim 1 further comprising adjusting the acoustic resonance frequency of the first resonant chamber.

14. A system for determining the presence of a constituent component in a sample fluid, the system comprising:

a source assembly, the source assembly produces electromagnetic energy with wavelengths in the infrared region;

a sample cell that holds a sample fluid, the sample cell has a first window that is substantially transparent to the electromagnetic energy, and the sample cell and source assembly arranged such that the electromagnetic energy propagates from the source assembly through the first window;

a detector assembly, distinct from the sample cell, the detector assembly in operational relationship to the electromagnetic energy that passes through the sample cell, the detector assembly comprising:

a first resonant chamber that defines an internal volume, the internal volume has an acoustic resonant frequency and at least a portion of the first resonant chamber is substantially transparent to the electromagnetic energy;

a detector fluid within the internal volume, the detector fluid has an electromagnetic absorption spectrum that overlaps an absorption spectrum of the constituent component; and a sensor coupled to the first resonant chamber, the sensor sensitive to acoustic energy in the first resonant chamber;

wherein the system determines the presence of the constituent component in the fluid sample based on the acoustic energy in the first resonant chamber.

15. The system of claim 14 further comprising a pressure vessel designed and constructed to be placed within a borehole, the pressure vessel houses the source assembly, sample cell and detector assembly.

16. The system of claim 15 wherein the pressure vessel is at least one selected from the group consisting of: the pressure vessel having threads which couple to a drill string; and the pressure vessel coupled to a cable such that the pressure vessel can be suspended within the borehole by the cable.

17. The system of claim 14 wherein source assembly creates electromagnetic energy with wavelengths between 1.5 micrometers (microns) and 25 microns inclusive.

18. The system of claim 14 wherein the source further comprises:

an electromagnetic energy source device that creates electromagnetic energy with wavelengths both within the infrared region, and outside the infrared region;

a filter in operational relationship to the electromagnetic energy source, the filter passes at least one wavelength between 1.5 micrometers (microns) and 25 microns inclusive, and blocks other wavelengths.

19. The system of claim 14 further comprising a modulation assembly within the optical path of the electromagnetic energy between the source assembly and the detector assembly, wherein the modulation assembly modulates the electromagnetic energy at a frequency substantially equal to the acoustic resonant frequency.

20. The system of claim 14 wherein the sample cell further comprises a portion of a fluid conduit, and wherein the electromagnetic energy is directed through the first window as the fluid sample flows through the fluid conduit.

21. The system of claim 20 wherein the sample cell is designed and constructed such that the flow rate of the fluid sample is substantially the same as the flow rate of the fluid sample in a flow line that feeds the sample cell.

22. The system of claim 14 wherein the sample cell further comprises a second window optically aligned with the first window, wherein the internal distance between the first and second windows is between 1 and 2 millimeters inclusive.

23. The system of claim 14 wherein the first resonant chamber is at least one selected from the group consisting of: cylindrical; elliptical; and parabolic.

24. The system of claim 14 wherein the first resonant chamber is cylindrical, and wherein the electromagnetic energy is focused on the center of the internal volume.

25. The system of claim 14 wherein the internal volume of the first resonant chamber is elliptical and has a first and second foci, and wherein the electromagnetic energy is focused on the first foci.

26. The system of claim 25 wherein the sensor is placed at the second foci.

27. The system of claim 14 wherein the detector assembly further comprises a plurality of sensors coupled to the first resonant chamber.

28. The system of claim 14 wherein the first resonant chamber further comprises an optical fiber having an exposed subwavelength taper portion, wherein at least a portion of the electromagnetic energy directed into the first resonant chamber propagates within the optical fiber.

29. A method comprising:

drawing a fluid sample from an earth formation into a tool that resides within a borehole that penetrates the earth formation; and then propagating electromagnetic energy into the fluid sample;

directing the electromagnetic energy that exits the fluid sample into a first resonant chamber, the first resonant chamber has an acoustic resonant frequency within the first resonant chamber;

absorbing at least a portion of the electromagnetic energy by a detector fluid within the first resonant chamber, the absorption creates acoustic energy in the first resonant chamber; and detecting amplitude of the acoustic energy within the first resonant chamber, the amplitude of the acoustic energy proportional to a concentration of a first constituent component in the fluid sample.

30. The method of claim 29 wherein propagating further comprises propagating the electromagnetic energy into the fluid sample as the fluid sample flows within the tool.

31. The method of claim 29 wherein propagating further comprises propagating electromagnetic energy having a wavelength between 1.5 micrometers (microns) and 25 microns inclusive.

32. The method of claim 29 wherein directing the electromagnetic energy further comprises directing the electromagnetic energy into the first resonant chamber with the detector fluid having an electromagnetic absorption spectrum that overlaps with an electromagnetic absorption spectrum of the first constituent component in the fluid sample.

33. The method of claim 29 wherein directing the electromagnetic energy further comprises directing the electromagnetic energy into the first resonant chamber containing the detector fluid comprising the first constituent component.

34. The method of claim 29 further comprising determining the concentration of the first constituent component in the fluid sample based on the amplitude of the acoustic energy.

35. The method of claim 29 further comprising:

wherein prior to directing the method further comprises splitting the electromagnetic energy into a first beam and second beam;

wherein directing further comprises directed the first beam of electromagnetic energy into the first resonant chamber;

directing the second beam of electromagnetic energy into a second resonant chamber, the second resonant chamber has an acoustic resonant frequency; and detecting amplitude of acoustic energy within the second resonant chamber, the amplitude of the acoustic energy in the second resonant chamber proportional to concentration of a second constituent component in the fluid sample.

36. The method of claim 35 further comprising:

determining the concentration of the first constituent component in the fluid sample based on the acoustic energy in the first resonant chamber; and determining the concentration of the second constituent component in the fluid sample based on the acoustic energy in the second resonant chamber.

37. The method of claim 29 further comprising:

directing electromagnetic energy that passes through the first resonant chamber into a second resonant chamber, the second resonant chamber has an acoustic resonant frequency; and detecting amplitude of acoustic energy within the second resonant chamber, the amplitude of the acoustic energy in the second resonant chamber proportional to concentration of a second constituent component in the fluid sample.

\* \* \* \* \*